US008796267B2

(12) United States Patent
Tung et al.

(10) Patent No.: US 8,796,267 B2
(45) Date of Patent: Aug. 5, 2014

(54) OXAZOLIDINONE DERIVATIVES AND METHODS OF USE

(75) Inventors: Roger Tung, Lexington, MA (US); Scott Harbeson, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 1070 days.

(21) Appl. No.: 12/214,260

(22) Filed: Jun. 17, 2008

(65) Prior Publication Data

US 2009/0093422 A1 Apr. 9, 2009

Related U.S. Application Data

(63) Continuation-in-part of application No. 11/877,666, filed on Oct. 23, 2007.

(60) Provisional application No. 60/853,890, filed on Oct. 23, 2006, provisional application No. 60/974,637, filed on Sep. 24, 2007.

(51) Int. Cl.
*A61K 31/5377* (2006.01)
*C07D 413/10* (2006.01)

(52) U.S. Cl.
USPC ........ 514/236.8; 544/106; 544/111; 544/137; 514/231.2; 514/231.5; 514/235.5

(58) Field of Classification Search
USPC .................. 548/215, 225, 229; 514/374, 376, 514/231.2, 231.5, 235.5, 236.8; 544/106, 544/111, 132, 137
See application file for complete search history.

(56) References Cited

U.S. PATENT DOCUMENTS

| | | | |
|---|---|---|---|
| 5,688,792 | A | 11/1997 | Barbachyn et al. |
| 5,880,118 | A | 3/1999 | Barbachyn et al. |
| 6,221,335 | B1 | 4/2001 | Foster |
| 6,239,152 | B1 | 5/2001 | Gordeev et al. |
| 6,255,304 | B1 | 7/2001 | Hester et al. |
| 6,277,985 | B1 | 8/2001 | Gadwood et al. |
| 6,440,710 | B1 | 8/2002 | Keinan et al. |
| 6,603,008 | B1 | 8/2003 | Ando et al. |
| 7,517,990 | B2 | 4/2009 | Ito et al. |
| 2005/0004118 | A1 | 1/2005 | Jilani |
| 2007/0082929 | A1 | 4/2007 | Gant et al. |
| 2007/0197695 | A1 | 8/2007 | Potyen et al. |
| 2008/0103122 | A1 | 5/2008 | Veltri |
| 2008/0139563 | A1 | 6/2008 | Tung et al. |
| 2008/0146573 | A1 | 6/2008 | Gant et al. |

FOREIGN PATENT DOCUMENTS

| | | |
|---|---|---|
| WO | WO 95/26325 | 10/1995 |
| WO | WO97/10223 | 3/1997 |
| WO | WO 2007/118651 A1 | 10/2007 |

OTHER PUBLICATIONS

Baillie, Thomas A., "The Use of Stable Isotopes in Pharmacological Research", *Pharmacological Reviews*, vol. 33, No. 2, pp. 81-132, 1981.
Browne, Thomas R., "Stable Isotope Techniques in Early Drug Development: An Economic Evaluation", *J. Clin. Pharmacol*, vol. 38, pp. 213-220, 1998.
Cherrah, et al., "Study of Deuterium Isotope Effects on Protein Binding by Gas Chromatography/Mass Spectrometry. Caffeine and Deuterated Isotopomers", *Biomedical and Environmental Mass Spectrometry*, vol. 14, pp. 653-657, 1987.
Dyck, et al., "Effects of Deuterium Substitution on the Catabolism of β-Phenylethylamine: An in Vivo Study", *Journal of Neurochemistry*, vol. 46, No. 2, pp. 399-404, 1986.
Ellermann, et al., "Effect of pentoxifylline on the ischemic rat kidney monitored by $^{31}P$ NMR spectroscopy in vivo," *Biomed. Biochim. Acta*, vol. 47, No. 6, pp. 515-521, 1988.
Fisher, et al., "The complexities inherent in attempts to decrease drug clearance by blocking sites of CYP-mediated metabolism," *Current Opinion in Drug Discovery & Development*, vol. 9, No. 1, pp. 101-109, 2006.
Foster, Allan B., "Deuterium isotope effects in studies of drug metabolism", *TIPS*, pp. 524-527, 1984.
Foster, Allan B., "Deuterium Isotope Effects in the Metabolism of Drugs and Xenobiotics: Implications for Drug Design", *Advances in Drug Research*, vol. 14, pp. 2-40, 1985.
Gouyette, et al., "Synthesis of Deuterium-labelled Elliptinium and its Use in Metabolic Studies", *Biomedical and Environmental Mass Spectrometry*, vol. 15, pp. 243-247, 1988.
Haskins, N.J., "The Application of Stable Isotopes in Biomedical Research", *Biomedical Mass Spectrometry*, vol. 9, No. 7, pp. 269-277, 1982.
Honma, et al., "Liberation of Deuterium from the Piperidine Ring during Hydroxylation", *Drug Metabolism and Disposition*, vol. 15, No. 4, pp. 551-559, 1987.
Kushner, et al., "Pharmacological uses and perspectives of heavy water and deuterated compounds", *Can. J. Physiol. Pharmacol.*, vol. 77, pp. 79-88, 1999.
Liu, Youhua, "Epithelial to Mesenchymal Transition in Renal Fibrogenesis: Pathologic Significance, Molecular Mechanism, and Therapeutic Intervention", *J. Am. Soc. Nephrol.*, vol. 15, pp. 1-12, 2004.
Pieniaszek, et al., "Moricizine Bioavailablity via Simultaneous, Dual, Stable Isotope Administration: Bioequivalence Implications", *The Journal of Clinical Pharmacology*, vol. 39, pp. 817-825, 1999.
Slatter, et al., "Pharmacokinetics, Metabolism, and Excretion of Linezolid following an Oral Dose of [$^{14}C$]Linezolid to Healthy Human Subjects", *Drug Metabolism and Disposition*, vol. 29, No. 8, pp. 1136-1145, 2001.
Slatter, et al., "Pharmacokinetics, toxicokinetics, distribution, metabolism and excretion of linezolid in mouse, rat and dog", *Xenobiotica*, vol. 32, No. 10, pp. 907-924, 2002.

(Continued)

*Primary Examiner* — Golam M M Shameem
(74) *Attorney, Agent, or Firm* — McCarter & English, LLP; Steven G. Davis; Emily A. Dertz

(57) ABSTRACT

This invention relates to novel N-[[3-[3-Fluoro-4-(4-morpholinyl)phenyl]-2-oxo-5-oxazolidinyl]methyl]-acetamide derivatives, their acceptable acid addition salts, solvates and hydrates. The invention also provides compositions comprising a compound of this invention and the use of such compositions in methods of treating diseases and conditions beneficially treated by antimicrobial agents.

10 Claims, 23 Drawing Sheets

(56) References Cited

OTHER PUBLICATIONS

Tonn, et al., "Simultaneous Analysis of Diphenhydramine and a Stable Isotope Analog ($^2H_{10}$)Diphenhydramine Using Capillary Gas Chromatography with Mass Selective Detection in Biological Fluids from Chronically Instrumented Pregnant Ewes", *Biological Mass Spectrometry*, vol. 22, pp. 633-642, 1993.

Wolen, Robert L., "The Application of Stable Isotopes to Studies of Drug Bioabailablity and Bioequivalence", *The Journal of Clinical Pharmacology*, vol. 26, pp. 419-424, 1986.

Prescribing information for Zyvox (Linezoid) *Pharmacia & UpJohn Company*, Revised Mar. 2007. pp. 1-34.

International Search Report issued in PCT Application No. PCT/US07/22516 on Oct. 16, 2008.

OXAZOLIDINONE DERIVATIVES AND METHODS OF USE

RELATED APPLICATIONS

This application is a continuation-in-part application of U.S. application Ser. No. 11/877,666, filed Oct. 23, 2007, which claims the benefit of U.S. provisional patent application Nos. 60/853,890, filed Oct. 23, 2006, and 60/974,637, filed Sep. 24, 2007. The contents of these applications are incorporated herein by reference in their entirety.

TECHNICAL FIELD OF THE INVENTION

This invention relates to novel N-[[3-[3-Fluoro-4-(4-morpholinyl)phenyl]-2-oxo-5-oxazolidinyl]methyl]-acetamide derivatives, their acceptable acid addition salts, solvates, and hydrates and thereof. The invention also provides compositions comprising a compound of this invention and the use of such compositions in methods of treating diseases and conditions beneficially treated by antimicrobial agents.

BACKGROUND OF THE INVENTION

Linezolid is the generic name for (S)—N-[[3-[3-Fluoro-4-(4-morpholinyl)phenyl]-2-oxo-5-oxazolidinyl]methyl]-acetamide. It has been shown to be effective in a number of animal models as an anti-microbial agent. The PK/PD relationship established in a mouse thigh infection model showed that the major parameter determining efficacy was the time above MIC. Linezolid is known to be a useful antimicrobial agent that is effective against a number of human and veterinary pathogens, including Gram-positive bacteria and certain Gram-negative and anaerobic bacteria. See U.S. Pat. No. 5,688,792 and International Application No. WO 95/07271.

In clinical trials, linezolid has been shown effective in the treatment of the following infections: Vancomycin-Resistant *Enterococcus faecium*; Nosocomial pneumonia due to *Staphylococcus aureus* and *Streptococcus pneumoniae*; complicated skin and skin structure infections caused by *Staphylococcus aureus, Streptococcus pyogenes*, or *Streptococcus agalactiae*; uncomplicated skin and skin structure infections caused by *Staphylococcus aureus* or *Streptococcus pyogenes*; and community-acquired pneumonia caused by *Streptococcus pneumoniae* or *Staphylococcus aureus*. (Barbachyn, M R et al., U.S. Pat. No. 5,688,792 to Pharmacia & Upjohn Co.; ZYVOX Label revised July 2006).

The recommended human dose is 600 mg every 12 hours for Vancomycin-resistant *Enterococcus faecium*, including bacteremia; nosocomial pneumonia; complicated skin and skin structure infections; and community-acquired pneumonia, including bacteremia. A dose of 400 mg BID is recommended for uncomplicated skin and skin structure infections. In clinical trials, this dose was shown to exceed the MIC90 for *Staphylococcus aureus* at trough. The PK/PD relationship in humans has not been clearly established. In one study, AUC/MIC was found to be the efficacy predictor; however, this PK/PD predictor was considered to be not reliable. Linezolid shows nonlinear kinetics at higher doses. Doses of 725 mg three times a day could not be tolerated due to an increase in serum creatinine. Myelosuppression has been reported in patients receiving linezolid. The myelosuppression is reversible and patients receiving linezolid should be monitored weekly. Although the PK/PD relationship for linezolid in humans is not well established, it would clearly be advantageous to identify a compound with a longer serum half-life that could maintain exposure levels above MIC at similar or lower doses. This would allow for a lower BID dose while maintaining the required MIC or for administration of higher dosage QD which would maintain the required MIC, while reducing AUC.

Metabolism of linezolid has been studied in mice, rats, dogs and humans where two major metabolic pathways have been identified. The major metabolites excreted are the carboxylic acids known as M4 and M6 resulting from hydrolysis of the lactone and lactam rings, respectively, that are formed by oxidations of the morpholine group. These metabolites are inactive. In humans, the principal metabolic pathway is the lactone pathway. See Slatter, J G et al., Xenobiotica 2002, 32, p. 907 and Drug Metab Dispos 2001, 29, p. 1136. Approximately 35% of an administered dose in humans is found in the urine as the parent compound while 50% of the dose is accounted for as the two metabolites. The oxidation of the morpholine ring is not due to Cyp enzymes. In vitro studies showed that linezolid is not a substrate, inhibitor, or inducer of clinically relevant Cyp isoforms (1A2; 2C9; 2C19; 2D6; 2E1; 3A4). See US NDA No. 02130.

The N-oxide of linezolid is also being investigated in preclinical trials as an anti-bacterial agent.

It is therefore desirable to create a compound displaying the beneficial activities of linezolid, that may also have other benefits, e.g., reduced adverse side effects, with a decreased metabolic liability, to further extend its pharmacological effective life, enhance patient compliance and, potentially, to decrease population pharmacokinetic variability and/or decrease its potential for dangerous drug-drug interactions.

BRIEF DESCRIPTION OF THE DRAWINGS

FIG. 7A is a plot showing plasma concentration of linezolid versus time following intravenous administration of linezolid and compound 101 for each male rat tested. FIG. 7B is a plot showing plasma concentration of linezolid versus time following oral administration of linezolid and compound 101 for each male rat tested. FIG. 7C is plot showing mean plasma concentration of linezolid versus time following intravenous and oral administration of compound 101 and linezolid. The number indication in the legend of each plot refer to the number associated with the male rat tested.

FIG. 8A is a plot showing plasma concentration of linezolid versus time following intravenous administration of linezolid and compound 103 for each male rat tested. FIG. 8B is a plot showing plasma concentration of linezolid versus time following oral administration of linezolid and compound 103 for each male rat tested. FIG. 8C is plot showing mean plasma concentration of linezolid versus time following intravenous and oral administration of compound 103 and linezolid. The number indication in the legend of each plot refer to the number associated with the male rat tested.

FIG. 9A is a plot showing plasma concentration of compound 101 versus time following intravenous administration of compound 101 and linezolid for each male rat tested. FIG. 9B is a plot showing plasma concentration of compound 101 versus time following oral administration of compound 101 and linezolid for each male rat tested. FIG. 9C is plot showing mean plasma concentration of compound 101 versus time following intravenous and oral administration of compound 101 and linezolid. The number indication in the legend of each plot refer to the number associated with the male rat tested.

FIG. 10A is a plot showing plasma concentration of compound 103 versus time following intravenous administration of compound 103 and linezolid for each male rat tested. FIG. 10B is a plot showing plasma concentration of compound 103 versus time following oral administration of compound 103 and linezolid for each male rat tested. FIG. 10C is plot showing mean plasma concentration of compound 103 versus time following intravenous and oral administration of compound 103 and linezolid. The number indication in the legend of each plot refer to the number associated with the male rat tested

DEFINITIONS

Figure 1:
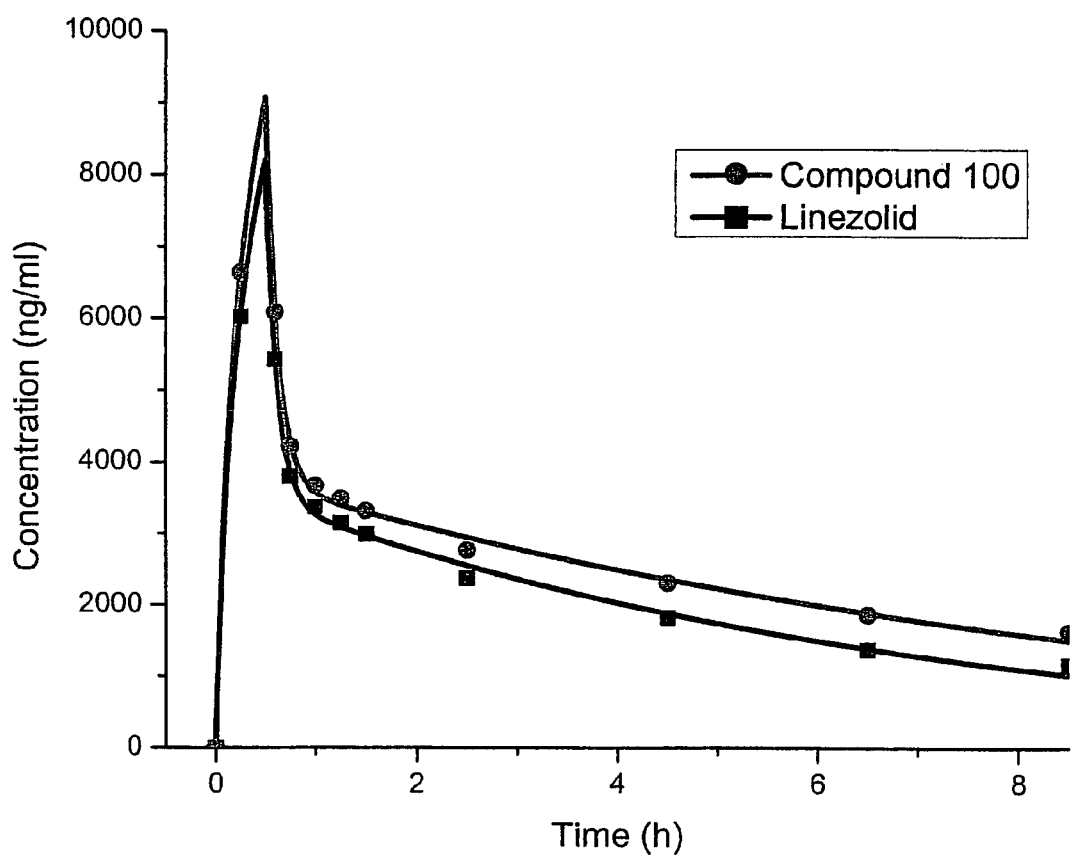
FIG. 1 depicts the serum pharmacokinetics of a combination of linezolid and Compound 100 following intravenous infusion into a female chimpanzee.

The terms "ameliorate" and "treat" are used interchangeably and both mean decrease, suppress, attenuate, diminish, arrest, or stabilize the development or progression of a disease (e.g., an infection, microbe).

By "disease" is meant any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of linezolid will inherently contain small amounts of deuterated and/or $^{13}$C-containing isotopologues. The concentration of naturally abundant stable hydrogen and carbon isotopes, notwithstanding this variation, is small and immaterial with respect to the degree of stable isotopic substitution of compounds of this invention. See for instance Wada E and Hanba Y, Seikagaku 1994 66: 15; Ganes L Z et al., Comp. Biochem. Physiol. A Mol. Integr. Physiol. 1998 119: 725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each atom designated as deuterium in Formula I or Ia of at least 3500 (52.5% deuterium incorporation at each atom designated as deuterium), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

In another embodiment, a "compound", as defined herein, contains less than 10%, preferably less than 6%, and more preferably less than 3% of all other isotopologues combined, including a form that lacks any deuterium or $^{13}$C. In certain aspects, the compound contains less than "X"% of all other isotopologues combined, including a form that lacks any deuterium or $^{13}$C; where X is any number between 0 and 10 (e.g., 1, 0.5, 0.001), inclusive. Compositions of matter that contain greater than 10% of all other isotopologues combined are referred to herein as "mixtures" and must meet the parameters set forth below. These limits of isotopic composition and all references to isotopic composition herein refer solely to the relative amounts of deuterium/hydrogen and $^{13}$C/$^{12}$C present in the active, free base form of the compound of Formula I/Ia, and do not include the isotopic composition of hydrolyzable portions of counterions.

The term "isotopologue" refers to species that differ from a specific compound of this invention only in the isotopic composition of their molecules or ions.

The term "compound" as used herein, is also intended to include salts, solvates, or hydrates, thereof. The specific recitation of "salt," "solvate," or "hydrate," in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present invention may contain one or more asymmetric carbon atoms. As such, a compound of this invention can exist as the individual stereoisomers (enantiomers or diastereomers) as well a mixture of stereoisomers. Accordingly, a compound of the present invention will include not only a stereoisomeric mixture, but also individual respective stereoisomers substantially free of other stereoisomers. The phrase "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to atypical antipsychotic agents).

Both "$^2$H" and "D" refer to deuterium. "Stereoisomer" refers to both enantiomers and diastereomers. "tert" refers to tertiary. "CDI" refers to 1,1'-carbonyldiimidazole.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Throughout this specification, reference to "each Y" includes, independently, all "Y" groups (e.g., $Y^1, Y^2, Y^3$, and $Y^4$) where applicable; "each W" includes, independently, all "W" groups (e.g., $W^1, W^2, W^3, W^4$, and $W^5$) where applicable; "each Z" includes, independently, all "Z" groups (e.g., $Z^1, Z^2, Z^3$, and $Z^4$) where applicable.

Therapeutic Compounds

The present invention provides a compound of formula I or Ia:

Formula (I)

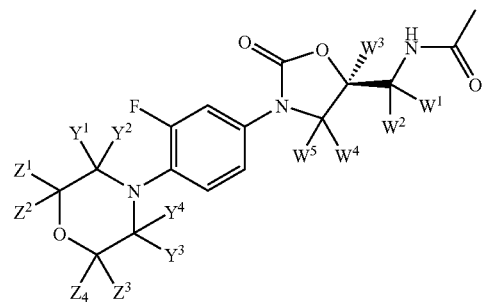

Formula (Ia)

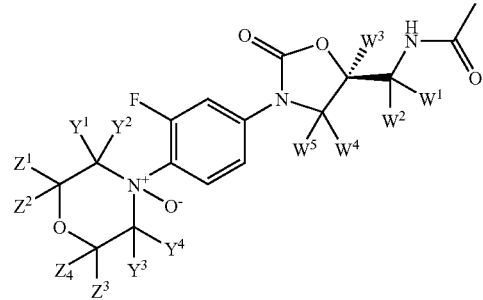

or a salt of Formula I; or a hydrate or solvate of Formula I or Ia, wherein:

each W is independently hydrogen or deuterium;

each Y is independently hydrogen or deuterium;

each Z is independently hydrogen, deuterium, or fluorine; and at least one W, Y or Z is deuterium.

In one embodiment at least one W is deuterium; at least two Y moieties are deuterium; and at least two Z moieties are deuterium or fluorine.

In one embodiment, $W^1$ and $W^2$ are simultaneously deuterium.

In one embodiment, $Y^1, Y^2, Y^3$ and $Y^4$ are simultaneously deuterium.

In one embodiment, each of $Z^1, Z^2, Z^3$ and $Z^4$ is independently selected from deuterium and fluorine. In a more specific embodiment, $Z^1, Z^2, Z^3$ and $Z^4$ are simultaneously deuterium.

In certain embodiments, the configuration of the compound of Formula I or Ia is (S).

In a more specific embodiment, $Y^1, Y^2, Y^3, Y^4, W^1$ and $W^2$ are simultaneously deuterium.

In another specific embodiment, each of $Z^1, Z^2, Z^3$ and $Z^4$ is independently selected from deuterium and fluorine; and $W^1$ and $W^2$ are simultaneously deuterium.

In another specific embodiment, $Y^1, Y^2, Y^3, Y^4, Z^1, Z^2, Z^3$ and $Z^4$ are simultaneously deuterium. In another specific embodiment, $Y^1, Y^2, Y^3, Y^4, Z^1, Z^2, Z^3$ and $Z^4$ are simultaneously deuterium; and $W^3, W^4$ and $W^5$ are simultaneously hydrogen.

In still another specific embodiment, $Z^1, Z^2, Z^3$ and $Z^4$ are simultaneously fluorine; and $Y^1, Y^2, Y^3$ and $Y^4$ are simultaneously deuterium.

In yet another specific embodiment $Y^1, Y^2, Y^3, Y^4, Z^1, Z^2, Z^3, Z^4, W^1$ and $W^2$ are simultaneously deuterium.

In another embodiment, $Z^1, Z^2, Z^3$ and $Z^4$ are simultaneously fluorine; and $Y^1, Y^2, Y^3, Y^4, W^1$, and $W^2$ are simultaneously deuterium.

In another specific embodiment, $Z^1, Z^2, Z^3$ and $Z^4$ are simultaneously deuterium; and $Y^1, Y^2, Y^3, Y^4, W^1$ and $W^2$ are simultaneously hydrogen. In another specific embodiment, $Z^1, Z^2, Z^3$ and $Z^4$ are simultaneously deuterium; and $W^3, W^4$ and $W^5$ are simultaneously hydrogen.

In still another specific embodiment, $Z^1, Z^2, Z^3, Z^4, Y^1, Y^2, Y^3$ and $Y^4$ are simultaneously deuterium; and $W^1$ and $W^2$ are simultaneously hydrogen.

In one embodiment, the compound of formula I or Ia contains at least three deuterium atoms.

In one embodiment, the compound of formula I or Ia contains at least four deuterium atoms.

In one embodiment, the compound of formula I or Ia contains at least five deuterium atoms.

Examples of specific compounds of this invention include:

Compound 100

Compound 101

Compound 102

Compound 103

Other examples of specific compounds of this invention include the following:

Compound 104

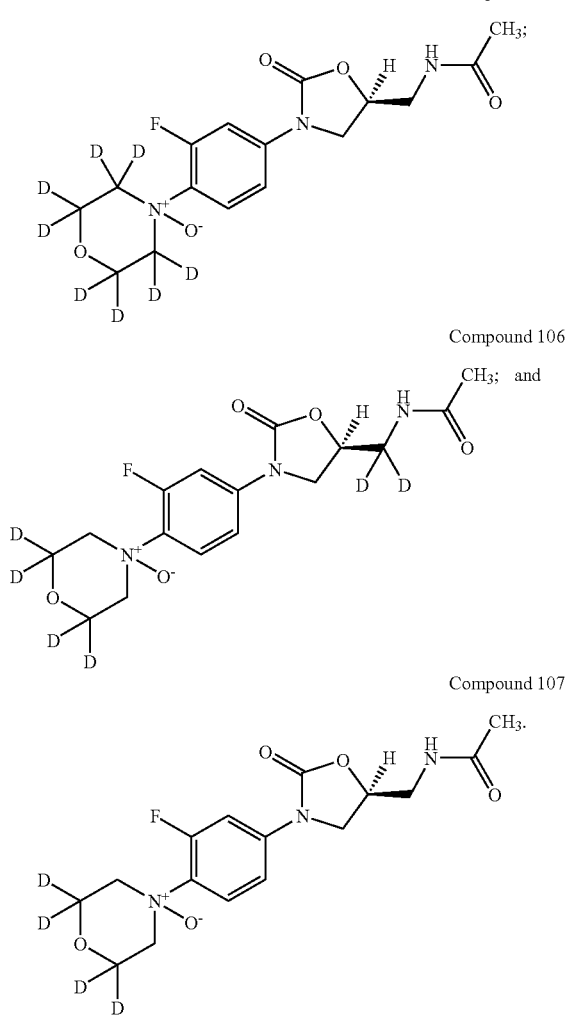

Compound 105

Compound 106 and

Compound 107

In another set of embodiments, any atom not designated as deuterium in any of the embodiments set forth above is present at its natural isotopic abundance.

General methods of incorporating deuterium in similar compounds are extensively documented. See, for instance, The Journal of Labelled Compounds and Radiopharmaceuticals (John Wiley & Sons), most issues of which contain detailed experimental descriptions on specific incorporation of deuterium into bioactive small organic molecules. See also, for instance, Leis H J Curr. Org. Chem. 1998 2: 131 and reference therein, and Moebius G, ZfI-Mitteilungen 1989 150: 297. Suitable commercial supplies of deuterium-labeled reagents include, among others, Isotec, Inc. (Miamisburg, Ohio); Cambridge Isotope Laboratories (Andover, Mass.); ICON Services Inc. (Summit, N.J.); and C/D/N Isotopes, Inc. (Pointe-Claire, Quebec, Canada).

The synthesis of compounds of formula I/Ia can be readily effected by synthetic chemists of ordinary skill by means known in the art of organic synthesis. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in PCT publications WO1997010223, WO2005099353, WO1995007271, WO2006008754; Lizondo, J et al., Drugs Fut 1996, 21(11): 1116; Brickner, S J et al., J Med Chem 1996, 39(3):673; and Mallesham, B et al., Org Lett 2003, 5(7):963. The scheme below illustrates how compounds of formula I or Ia may be prepared.

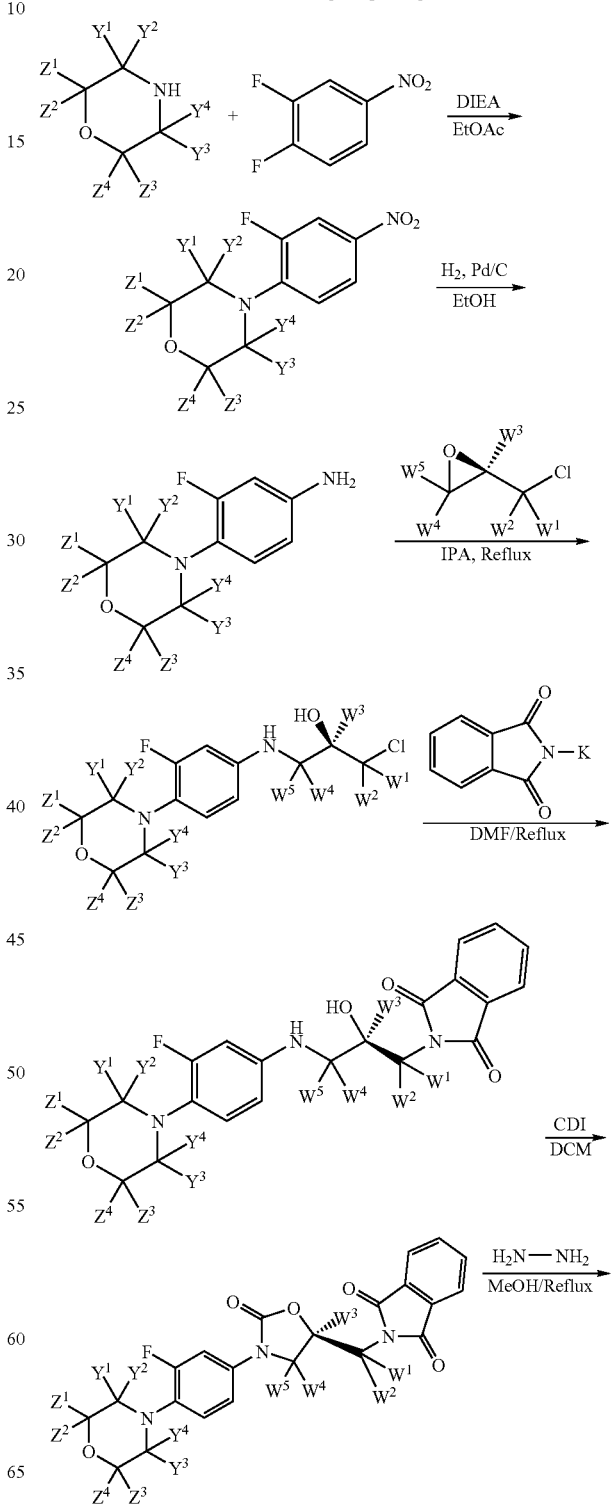

Scheme 1. General Route for Preparing Compounds of Formula I

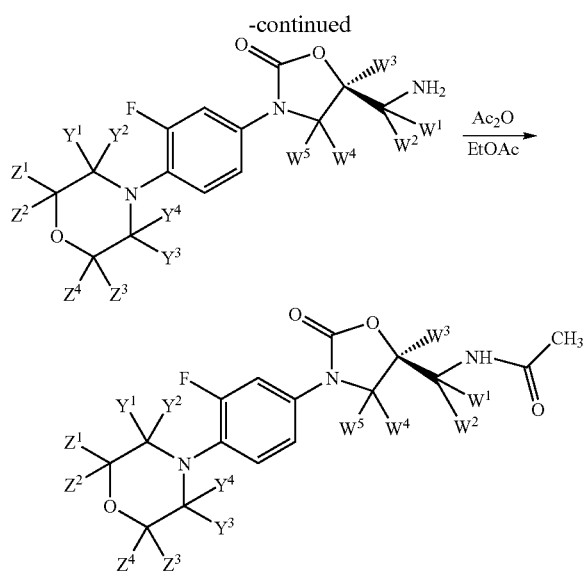

Scheme 1 above shows a general route for preparing compounds of formula I. Compounds of formula Ia can be made from Formula I compounds using a suitable oxidant such as pertrifluoroacetic acid or m-chloroperbenzoic acid. See WO 1997010223. Other approaches to synthesizing compounds of formula I/Ia are set forth in the examples or can readily be adapted from references cited herein. Variations of these procedures and their optimization are within the skill of the ordinary practitioner The specific approaches and compounds shown above are not intended to be limiting. Additional methods of synthesizing compounds of formula I/Ia and their synthetic precursors, including those within routes not explicitly shown in Schemes herein, are within the means of chemists of ordinary skill in the art. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, 2$^{nd}$ Edition, Carlson R, Ed, 2005; Elsevier Science Ltd.; Jähnisch, K et al, Angew. Chem. Int. Ed. Engl. 2004 43: 406; and references therein). In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the US Patent and Trademark Office text database. The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The synthetic methods described herein may also additionally include steps, either before or after any of the steps described in the preceding Scheme, to add or remove suitable protecting groups in order to ultimately allow synthesis of the compound of the formulae described herein. The methods delineated herein contemplate converting compounds of one formula to compounds of another formula. The process of converting refers to one or more chemical transformations, which may be performed in situ, or with isolation of intermediate compounds. The transformations may include reacting the starting compounds or intermediates with additional reagents using techniques and protocols known in the art, including those in the references cited herein. Certain intermediates may be used with or without purification (e.g., filtration, distillation, sublimation, crystallization, trituration, solid phase extraction, and chromatography).

Combinations of substituents and variables envisioned by this invention are only those that result in the formation of stable compounds.

Compositions

The invention also provides compositions comprising an effective amount of a compound of Formula I/Ia (e.g., including any of the formulae herein), or a pharmaceutically acceptable salt of Formula I; or a hydrate or solvate of Formula I or Ia; and an acceptable carrier. In one embodiment, the composition is pyrogen-free. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Such administration is known to be effective with erectile dysfunction drugs: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters.

Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of the present invention further comprises a second therapeutic agent. The second therapeutic agent includes any compound or therapeutic agent known to have or that demonstrates advantageous properties when administered with an antimicrobial compound, in particular, in anti-microbial therapy, combination therapy with other anti-microbial and/or anti-inflammatory agents is envisaged. Combination therapies according to the present invention thus include the administration of at least one compound of formula I or Ia, as well as optional use of other anti-microbial agents and optional use of cyclooxygenase inhibitors, particularly selective inhibitors of cyclooxygenase-2. Other anti-microbial therapies and anti-inflammatory agents are described for instance in International Publication No.s WO 01/34128 and WO 03/061704, which applications are incorporated by reference to the extent that they disclose combinations of anti-microbial and anti-inflammatory therapies.

Examples of second therapeutic agents that may be formulated with a compound of this invention include, but are not limited to, gentamicin, tobramycin, aztreonam, cefazolin, ceftazidime, piperacillin, ciprofloxacin, ofloxacin, levofloxacin, celecoxib, and rofecoxib.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

The compounds of the present invention demonstrate a longer half-life, and produce a higher serum concentration level 24 hours post-dosing as compare to the same amount of linezolid on a mole basis. Thus in one embodiment, the invention provides a pharmaceutical composition comprising an effective amount of a compound of formula I, the administration of which to a test subject results in a serum terminal elimination half-life of the compound that is greater than the serum terminal elimination half-life of linezolid when linezolid is administered to an equivalent test subject in a pharmaceutical composition comprising an amount of linezolid that is the same as the amount of the compound of formula I on a mole basis of active ingredient and that is administered in the same dosing regimen as the compound of formula I. In other embodiments, the serum terminal elimination half-life of a compound of formula I is at least 125%, 130%, 135%, 140% or more of the serum terminal elimination half-life of linezolid produced by a corresponding linezolid composition administered in the same dosing regimen.

In a related embodiment, the invention provides a pharmaceutical composition comprising an effective amount of a compound of formula I, or a pharmaceutically acceptable salt thereof, wherein the serum terminal elimination half-life of the compound following administration of a single dose of the first composition to a test subject is greater than 7 hours.

In another embodiment, the invention provides a pharmaceutical composition comprising an effective amount of a compound of formula I, the administration of which to a test subject results in a serum concentration of the compound 24 hours post-administration that is greater than the serum concentration of linezolid 24 hours post-administration when linezolid is administered to an equivalent test subject in a pharmaceutical composition comprising an amount of linezolid that is the same as the amount of the compound of formula I on a mole basis of active ingredient and that is administered in the same dosing regimen as the compound of formula I. In other embodiments, the serum concentration of a compound of formula I produced 24 hours post-administration of a composition of this invention is at least 150%, 175%, 200%, 225%, 250%, 275%, 300% or more of the serum concentration of linezolid produced by a corresponding linezolid composition administered in the same dosing regimen.

In one embodiment, the invention provides a pharmaceutical composition comprising an effective amount of a compound of formula I, the administration of which to a test subject results in an $AUC_{0-24}$ of the compound that is greater than the $AUC_{0-24}$ of linezolid when linezolid is administered to an equivalent test subject in a pharmaceutical composition comprising an amount of linezolid that is the same as the amount of the compound of formula I on a mole basis of active ingredient and that is administered in the same dosing regimen as the compound of formula I. In other embodiments, the $AUC_{0-24}$ produced by a composition of this invention is at least 125%, 130%, 135%, 140%, 145% or more of the $AUC_{0-24}$ produced by a corresponding linezolid composition administered in the same dosing regimen.

The compounds of the present invention also demonstrate greater resistance to certain metabolism as compared to linezolid. Thus, in another embodiment, the invention provides a pharmaceutical composition comprising an effective amount of a compound of formula I, wherein the amount of the compound excreted intact in 24 hours following administration to a test subject is greater than the amount of linezolid excreted intact in 24 hours following administration of linezolid to an equivalent test subject in a pharmaceutical composition comprising an amount of linezolid that is the same as the amount of the compound of formula I on a mole basis of active ingredient and that is administered in the same dosing regimen as the compound of formula I. In other embodiments, the amount of a compound of formula I excreted intact in 24 hours following administration of a composition of this invention is at least 150%, 160%, 170%, 180%, 190%, 200%, 210% or more of the amount of linezolid excreted intact 24 hours following administration of a corresponding linezolid composition administered in the same dosing regimen.

In a related embodiment, the invention provides a pharmaceutical composition comprising an effective amount of a compound of formula I, or a pharmaceutically acceptable salt thereof, wherein in 24 hours following administration of the composition to a subject, at least 45% of the effective amount of the compound is excreted intact by the subject.

In yet another embodiment, the invention provides a pharmaceutical composition comprising an effective amount of a compound of formula I, the administration of which to a test subject results in one or more of: a) a similar $AUC_{0-24}$; b) a similar $C_{max}$; or c) a similar $C_{min}$ as linezolid when linezolid is administered to an equivalent test subject in a pharmaceutical composition comprising an amount of linezolid that is greater than the amount of the compound of formula I on a mole basis of active ingredient and that is administered in the same dosing regimen as the compound of formula I. In other embodiments, the effective amount of a compound of formula I is less than 80%, 70%, 60%, 50%, 40%, 33%, or less of the amount of linezolid required to produce one or more of a) a similar $AUC_{0-24}$; b) a similar $C_{max}$; or c) a similar $C_{min}$ when administered in the same dosing regimen as the compound of formula I.

In yet another embodiment, the invention provides a pharmaceutical composition comprising an effective amount of a compound of formula I, the administration of one or more dosages of which to a test subject results in a) maintenance of a serum concentration of the compound at more than 6 mg/L for 24 hours following administration of the first dosage; and b) an $AUC_{0-24}$ of the compound that is less than the $AUC_{0-24}$ of linezolid when linezolid is administered to an equivalent test subject in a pharmaceutical composition comprising an amount of linezolid required to maintain a serum level of linezolid of more than 6 mg/L for 24 hours following administration. In other embodiments, the $AUC_{0-24}$ produced by a composition of this invention is less than 85%, 80%, 75%, 70%, 65%, or less of the $AUC_{0-24}$ produced by the required dosages of the linezolid composition.

In each of the above embodiments, a pharmaceutically acceptable salt of a compound of formula I, and/or linezolid may be used instead of the free base form.

In a more specific embodiment, in each of the compositions set forth above, the compound is selected from compound 100, compound 101, compound 102 or compound 103.

A "test subject" is any mammal, preferably a human.

An "equivalent test subject" is defined herein as being of the same species and sex as the test subject, and which shows no more than 10% variability as compared to the test subject in the pharmacokinetic parameter being tested after administration of an equal amount of linezolid to both the test subject and the equivalent subject.

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardsley, N.Y., 1970, 537.

Because the compounds of the present invention demonstrate a longer serum half-life than linezolid at equal dosages, they can be administered at lower doses and/or at less frequent intervals than linezolid while still maintaining the required time above minimum inhibitor concentration ("MIC"). As compared with linezolid, less frequent intervals of administration of the compounds of the present invention will reduce the number of spikes in serum concentration that are associated with each dosing. This, in turn, will reduce the patient's total exposure to the compound of this invention over time (cumulative AUC exposure). It is this cumulative AUC exposure that has been implicated in linezolid's progressive toxicity, which is believed to be caused by its inhibition of mitochondrial protein synthesis (Devriese A S et al., Clin Infect Dis 2006, 42:1111). Linezolid's progressive toxicity limits the amount of time that a patient can take the drug.

The reduction in cumulative AUC exposure as compared to linezolid can be further enhanced through the use of controlled release formulations comprising a compound of this invention. Such controlled release formulations are prepared using methods well-known in the art; see e.g. Remmington: The Science and Practice of Pharmacy, $21^{st}$ edition (Lippincott Williams & Wilkins 2005); and Modern Pharmaceutics $4^{th}$ Edition (Drugs and the Pharmaceutical Sciences Vol. 121), Banker G S and Rhodes C T editors (Informa Healthcare 2002).

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardsley, N.Y., 1970, 537. An effective amount of a compound of this invention can range from about 50 mg to about 2000 mg every 24 hours, if appropriate in the form of several individual doses. In one embodiment the effective amount of a compound of this invention ranges from about 250 mg to about 1250 mg every 24 hours in the form of a single dosage or two separate dosages of about 125 mg to about 625 mg each given every 12 hours. In another embodiment the effective amount of a compound of this invention ranges from about 750 mg to about 1250 mg every 24 hours in the form of a single dosage or two separate dosages of about 375 mg to about 625 mg each given every 12 hours. In still another embodiment the effective amount of a compound of this invention ranges from about 450 mg to about 1200 mg every 24 hours in the form of a single dosage or two separate dosages of about 225 mg to about 625 mg each given every 12 hours. In a more specific embodiment the effective amount of a compound of this invention ranges from about 450 mg to about 750 mg every 24 hours in the form of a single dosage or two separate dosages of about 225 mg to about 375 mg each given every 12 hours. Other ranges of a compound of this invention that fall within or between any of the above-recited ranges are also within the scope of the invention. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

The milligram amounts of compounds present in the pharmaceutical compositions of the present invention and for use in the methods of the present invention represent the amount of free base compound. It will be understood that the use of pharmaceutical salts of the compounds of the present invention will require that the stated amounts be increased so that a mole equivalent of the free base compound is used.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from or susceptible to a disease that is beneficially treated by linezolid comprising the step of administering to said subject an effective amount of a compound or a composition of this invention. Such diseases are well known in the art and include for instance, the treatment or prevention of a variety of disease states typically treated by antimicrobial therapy (e.g., infection, fungal disorders). The compounds of formula I/Ia, therefore, have utility in the treatment of disorders including those mediated by Gram-positive bacteria and certain Gram-negative and anaerobic bacteria.

In one embodiment, the invention provides a method of treating a subject suffering from or susceptible to an infection caused by a bacteria selected from *Enterococcus faecium, Staphylococcus aureus, Streptococcus agalactiae, Streptococcus pneumoniae, Streptococcus pyrogenes, Enterococcus faecalis, Staphylococcus epidermidis, Staphyloccocus haemolyticus,* and *Pasteurella multocida,*

In another embodiment, the invention provides a method of treating a subject suffering from or susceptible to a disease or disorder (or symptoms thereof) selected from a Gram-positive bacterial infection, Vancomycin-resistant *Enterococcus faecium* infection; nosocomial pneumonia due to *Staphylococcus aureus* and *Streptococcus pneumoniae*; complicated skin and skin structure infections caused by *Staphylococcus aureus, Streptococcus pyogenes*, or *Streptococcus agalactiae*; uncomplicated skin and skin structure infections caused by *Staphylococcus aureus* or *Streptococcus pyogenes*; community-acquired pneumonia caused by *Streptococcus pneumoniae* or *Staphylococcus aureus*; and tuberculosis.

In another embodiment, the invention provides a method of treating a subject suffering from or susceptible to a disease or disorder (or symptoms thereof) selected from a Gram-positive bacterial infection, Vancomycin-resistant *Enterococcus faecium* infection; nosocomial pneumonia due to *Staphylococcus aureus* and *Streptococcus pneumoniae*; complicated skin and skin structure infections caused by *Staphylococcus aureus, Streptococcus pyogenes*, or *Streptococcus agalactiae*; uncomplicated skin and skin structure infections caused by *Staphylococcus aureus* or *Streptococcus pyogenes*; and community-acquired pneumonia caused by *Streptococcus pneumoniae* or *Staphylococcus aureus*.

The method of the present invention may also be employed with other therapeutic methods of microbial infection treatment. In particular, in anti-microbial therapy, combination therapy with other anti-microbial and/or anti-inflammatory agents is envisaged. The administration of at least one compound of formula I or Ia as well as optional use of other anti-microbial agents and optional use of cyclooxygenase inhibitors, particularly selective inhibitors of cyclooxygenase-2. Such combination of agents may be administered together or separately and, when administered separately this may occur simultaneously or sequentially in any order, both close and remote in time. Other anti-microbial therapies and anti-inflammatory agents are described for instance in International Publication Nos. WO 01/34128 and WO 03/061704, which applications are incorporated by reference to the extent that they disclose combinations of anti-microbial and anti-inflammatory therapies.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, the invention provides a method of modulating the activity of a cell comprising contacting a cell with one or more compounds of any of the formulae herein.

In another embodiment, the invention provides a method of treating a patient suffering from or susceptible to a bacterial infection comprising the step of administering to the patient in need thereof over a 24 hour period between about 450 mg and about 750 mg of a compound of formula I or Ia. In another embodiment the patient is administered between 450 mg and 700 mg of a compound of formula I or Ia.

In another embodiment, the above method produces a steady state $C_{min}$ of greater than about 3 mg/L. In another embodiment, the above method produces a steady state $C_{min}$ of greater than about 4 mg/L. In another embodiment, the above method produces a steady state $C_{min}$ of greater than about 6 mg/L. In still another embodiment, the above method produces a steady state $C_{max}$ of less than about 18 mg/L. In another embodiment, the above method produces a steady state $C_{max}$ of less than about 16 mg/L. In another embodiment, the above method produces a steady state $C_{max}$ of less than about 13 mg/L. In still another embodiment, the above method produces a steady state $C_{max}$ of less than about 11.5 mg/L.

In another embodiment, the above method of treatment comprises the further step of co-administering to the patient one or more second therapeutic agents. The choice of second therapeutic agent may be made from any second therapeutic agent known to be useful for co-administration with linezolid.

In a specific embodiment, the combination therapies of this invention include co-administering a compound of Formula I and a second therapeutic agent selected from gentamicin, tobramycin, aztreonam, cefazolin, ceftazidime, piperacillin, ciprofloxacin, ofloxacin, levofloxacin, celecoxib, and rofecoxib.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of formula I or Ia alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

Diagnostic Methods and Kits

The compounds and compositions of this invention are also useful as reagents in methods for determining the concentration of linezolid in solution or biological sample such as plasma, examining the metabolism of linezolid and other analytical studies.

According to one embodiment, the invention provides a method of determining the concentration, in a solution or a biological sample, of linezolid, comprising the steps of:
 a) adding a known concentration of a compound of Formula I or Ia to the solution of biological sample;
 b) subjecting the solution or biological sample to a measuring device that distinguishes linezolid from the compound of Formula I or Ia;
 c) calibrating the measuring device to correlate the detected quantity of the compound of Formula I or Ia with the known concentration of the compound of Formula I or Ia added to the biological sample or solution; and
 d) measuring the quantity of linezolid in the biological sample with said calibrated measuring device; and
 e) determining the concentration of linezolid in the solution of sample using the correlation between detected quantity and concentration obtained for a compound of Formula I or Ia.

Measuring devices that can distinguish linezolid from the corresponding compound of Formula I or Ia include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I or Ia comprising the steps of contacting the compound of Formula I or Ia with a metabolizing enzyme source for a period of time and comparing the amount of the compound of Formula I or Ia with the metabolic products of the compound of Formula I or Ia after the period of time.

In a related embodiment, the invention provides a method of evaluating the metabolic stability of a compound of Formula I or Ia in a patient following administration of the compound of Formula I or Ia. This method comprises the steps of obtaining a serum, urine or feces sample from the patient at a period of time following the administration of the compound of Formula I or Ia to the subject; and comparing the amount of the compound of Formula I or Ia with the metabolic products of the compound of Formula I or Ia in the serum, urine or feces sample.

The present invention also provides kits for use to treat an infectious disease or disorder, including those delineated herein. These kits comprise: a) a pharmaceutical composition comprising a compound of Formula I/Ia or a salt of Formula I; or a hydrate or solvate of Formula I or Ia, wherein said pharmaceutical composition is in a container; and b) instructions describing a method of using the pharmaceutical composition to treat an infectious disease or disorder, including those delineated herein.

The container may be any vessel or other sealed or sealable apparatus that can hold said pharmaceutical composition. Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kit may additionally comprise a memory aid of the type containing information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information. For single dose dispensers, memory aids further include a mechanical counter which indicates the number of daily doses that have been dispensed and a battery-powered micro-chip memory coupled with a liquid crystal readout and/or audible reminder signal which, for example, reads out the date that the last daily dose has been taken and/or reminds one when the next dose is to be taken. Other memory aids useful in such kits are a calendar printed on a card, as well as other variations that will be readily apparent.

EXAMPLES

Example 1

Synthesis of Intermediate 12

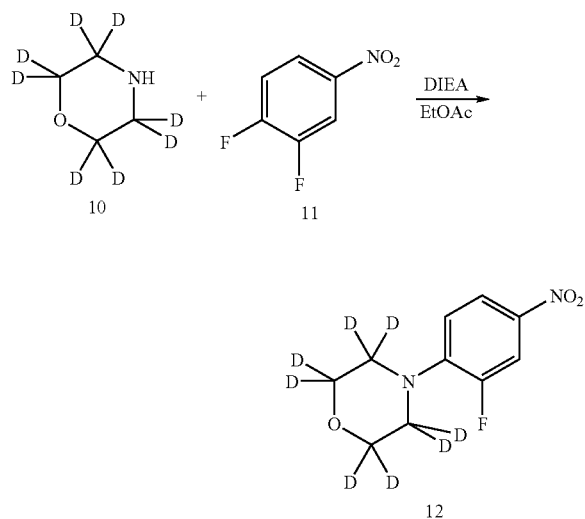

To a stirred solution of $d_8$-morpholine (10; 23.5 g, 0.25 mol) and $^i$Pr$_2$EtN (44 ml, 0.25 mol) in ethyl acetate ("EtOAc") (140 ml), cooled in an ice bath, was added 3,4-difluoronitrobenzene (11, 27.4 ml, 0.25 mol), dropwise over 10 min. The reaction mixture was stirred for 48 h at room temperature. The reaction mixture was diluted with EtOAc (300 ml) and CH$_2$Cl$_2$ (50 ml) then water (350 ml) was added. The layers were separated and the aqueous layer washed with EtOAc (3×300 ml). The combined organics were dried (MgSO$_4$), filtered and concentrated in vacuo. The crude product was purified using column chromatography (1 kg silica) eluting with 20% EtOAc/hexane to give the intermediate 12 in 87% yield.

Example 2

Synthesis of Intermediate 13

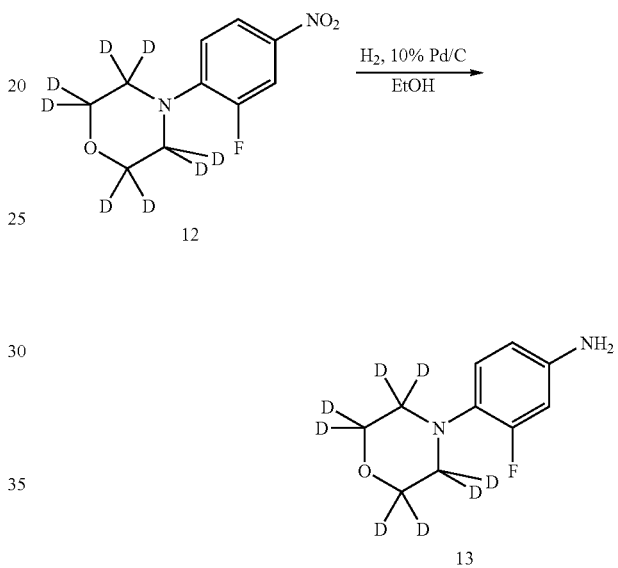

To a stirred suspension of 12 (50 g, 0.21 mol) in denatured EtOH (875 ml) under N$_2$ was added 10% Pd/C (50% wet, 17.5 g). The reaction vessel was purged with N$_2$ for 10 min, H$_2$ for 10 min and stirred overnight under an atmosphere of H$_2$. Hydrogenation was stopped and the vessel purged with N$_2$ for 15 min. The mixture was filtered through Celite, washed through with denatured EtOH (500 ml) and DCM (3×700 ml). The combined filtrates were concentrated in vacuo to give the desired aniline 13 (38.5 g, 90% yield) as a pink solid.

Example 3

Synthesis of (R)-d$_2$-epichlorohydrin 14B

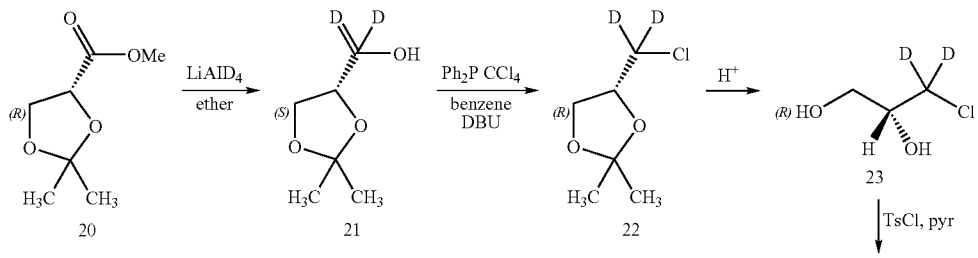

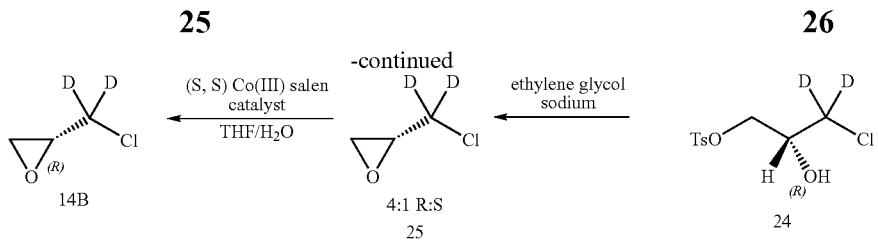

To an ice-cooled solution of methyl-α,β-isopropylidene-D-glycerate (20; 175 g, 1.09 mol, 1 equiv) in Et$_2$O (1000 ml) was added LiAlD$_4$ (34.43 g, 0.82 mol, 0.75 equiv) as a suspension in Et$_2$O (1000 ml) over 3 h. The reaction mixture was refluxed for 5 h. The mixture was allowed to cool to room temperature, diluted with Et$_2$O (1000 ml) and quenched with water (40 ml). The mixture was stirred for 15 min, filtered and the solid washed with Et$_2$O (1000 ml). The filtrate was concentrated in vacuo to give the corresponding alcohol 21 in high purity (121.3 g, 83% yield).

The alcohol (21; 60.65 g, 0.45 mol, 1 equiv) was dissolved in benzene (110 ml) together with PPh$_3$ (124 g, 0.47 mol, 1.05 equiv) and DBU (34 ml, 0.225 mol, 0.5 equiv). The mixture was added dropwise over 30 min to a refluxing solution of CCl$_4$ (110 ml) containing DBU (17 ml, 0.11 mol, 0.25 equiv). The reaction mixture was stirred at reflux overnight. The reaction mixture was allowed to cool to room temperature and concentrated in vacuo to give a crude mixture. The crude mixture was absorbed onto silica (60 g) and purified using column chromatography (silica: 1200 g) eluting with EtOAc: hexane 1:1 to give the desired chloride 22 in 54% yield.

The chloride 22 (37.6 g, 0.25 mol) was added to a solution of acetone (60 ml) and 1M HCl (150 ml). The mixture was heated to 55° C. for 30 min. The reaction mixture was allowed to cool to room temperature and the acetone removed in vacuo. The mixture was saturated with NaCl (43 g) and extracted with EtOAc (2×250 ml). The combined EtOAc layers were dried over MgSO$_4$ and concentrated to give the diol, (R)-d$_2$-chlorohydrin 23 (21.8 g, 79% yield).

To an ice-cooled solution of (R)-d$_2$-chlorohydrin 23 (21.0 g, 0.19 mol, 1 equiv) in pyridine (210 ml) was added portionwise toluenesulfonyl chloride (35.5 g, 0.19 mol, 1 equiv). After complete addition of the sulfonyl chloride the mixture was allowed to warm to room temperature and stirred for 1 h. Added to the mixture was Et$_2$O (300 ml) and the mixture washed with 1M HCl (3×500 ml) until the aqueous wash was acidic. The organic extract was washed with sat.aq. NaHCO$_3$ (300 ml), dried over MgSO$_4$ and concentrated to give the corresponding tosylate 24 (31.3 g, 63% yield).

Sodium metal (5 g, 37.48 mmol, 2 equiv) was added to ethylene glycol (40 ml), and the mixture stirred at 20° C. overnight to produce a solution of sodium ethylene glycolate in ethylene glycol. A solution of tosylate 24 (5 g, 18.74 mmol, 1 equiv) in ethylene glycol (5 ml) was then added, and the mixture stirred at 20° C. for 15 min. The product was removed from the mixture under reduced pressure and collected in a dry ice/IPA cold finger as a clear liquid to give enantiomerically enriched (R)-d$_2$-epichlorohydrin 25 (1.02 g, 58% yield). Chiral GC indicated an enantiomeric excess of 79.4%.

The (S,S)-Cobalt (II) catalyst (43.2 mg, 0.0716 mmol) was dissolved in toluene (8 µl). Acetic acid (8.6 µl, 0.143 mmol, 2 equiv) was added and the resulting mixture was stirred open to air at room temperature for 30 min, during which time the colour of the mixture changes from orange to dark brown. All volatile materials were removed in vacuo, affording the acetate complex of the Cobalt (III) catalyst as a brown residue. Added to the prepared catalyst was 80% enantiomerically enriched (R)-d$_2$-epichlorohydrin 25 (2.5 g) and THF (2.5 ml). The reaction flask was cooled to 0° C., and H$_2$O (0.05 ml) was added dropwise over 15 min. The reaction was allowed to warm to room temperature and stirred for 18 h. Added to the reaction mixture was a portion of MgSO$_4$ and the (R)-d$_2$-epichlorohydrin 26 was isolated by distillation at room temperature to give a 1:1 mix of epichlorohydrin and THF. Chiral GC analysis indicated an ee of 99.1%.

Example 4

Synthesis of Intermediates 15A and 15B

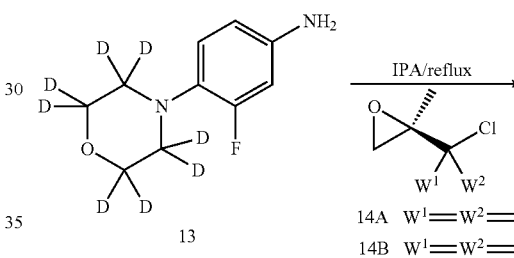

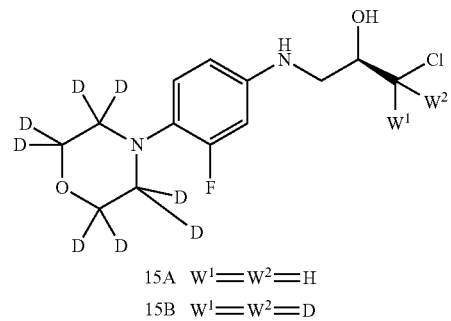

Aniline 13 (15 g, 74 mmol, 1.0 equiv.) was dissolved in isopropanol (75 ml) under N$_2$, and (R)-epichlorohydrin (14A; 7.0 g, 81.4 mmol, 1.1 equiv.) added. The mixture was stirred at reflux overnight. The solvent was removed in vacuo and the residue purified by column chromatography (750 g silica, CH$_2$Cl$_2$, then 1% MeOH, CH$_2$Cl$_2$) to give 15A as a pale brown oil (12.8 g, 58% yield).

Aniline (4.1 g, 20.1 mmol, 1.0 equiv.) was dissolved in isopropanol (20 ml) under N$_2$, and (R)-d$_2$-epichlorohydrin (14B; 2.0 g, 22.1 mmol, 1.1 equiv.) added. The mixture was stirred at reflux overnight. The solvent was removed in vacuo and the residue purified by column chromatography (300 g silica, CH$_2$Cl$_2$, then 1% MeOH, CH$_2$Cl$_2$) to give 15B as a pale brown oil (3.0 g, 50% yield). LC indicated a purity of 97%. Chiral LC indicated an enantiomeric excess of 95.7%.

Example 5

Synthesis of Intermediates 17A and 17B

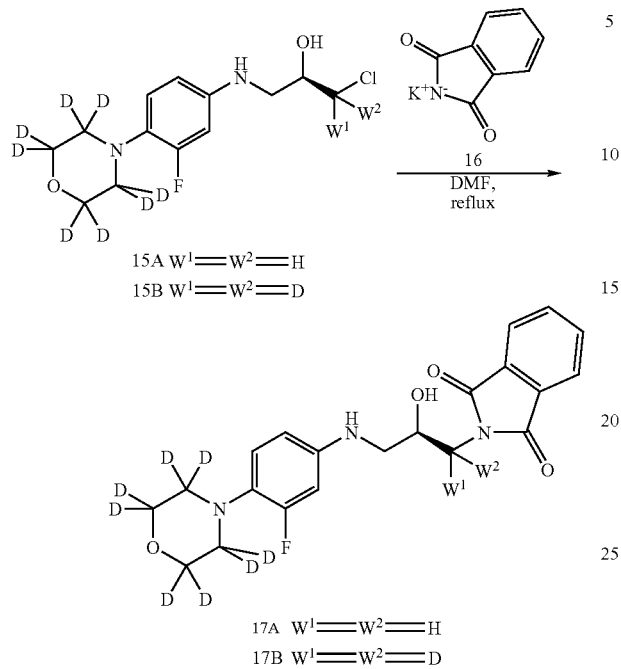

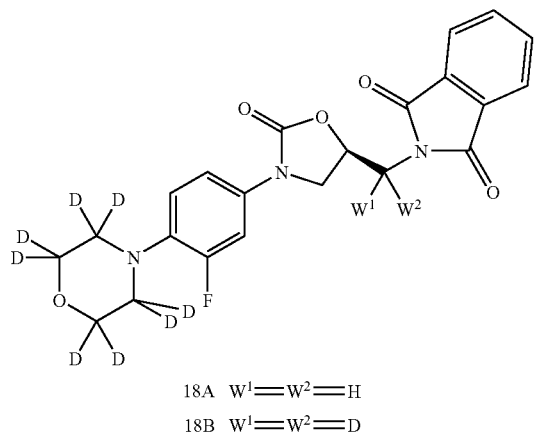

Intermediate 15A (12.8 g, 0.043 mol, 1 equiv), potassium phthalimide (16; 10.4 g, 0.056 mol, 1.3 equiv) and DMF (100 ml) was heated to 100° C. for 5 h. LC analysis indicated complete reaction. The reaction mixture was cooled to room temperature and poured into water (450 ml). The mixture was stirred for 2 h, filtered and the solid cake dried in a vacuum oven at 40° C. overnight to give 17B (9 g, 51% yield). LCMS indicated a purity of 95.0%.

Intermediate 15B (3.2 g, 10.7 mmol, 1 equiv), potassium phthalimide (16; 2.58 g, 13.9 mmol, 1.3 equiv) and DMF (23 ml) was heated to 100° C. for 5 h. The reaction mixture was cooled to room temperature and poured into water (100 ml). The mixture was stirred for 2 h, filtered and the solid cake dried in a vacuum oven at 40° C. overnight to give 17B (2.27 g, 52% yield). LC indicated a purity of 98.2%. Chiral LC indicated an enantiomeric excess of 98.6%.

Example 6

Synthesis of Intermediates 18A and 18B

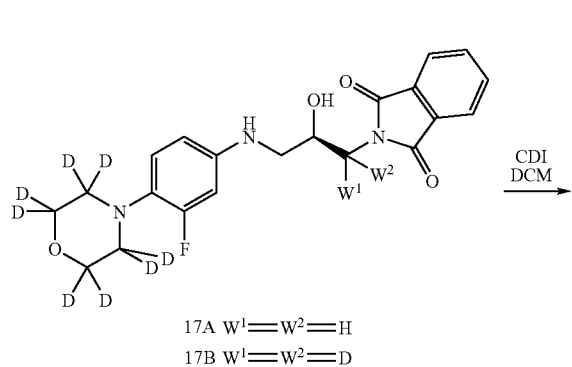

Intermediate 17A (9.0 g, 22 mmol, 1 equiv) was dissolved in DCM (100 ml), carbonyl diimidazole (5.0 g, 31 mmol, 1.4 equiv) was added at room temperature and the mixture was stirred overnight under nitrogen. LC analysis indicated the reaction was complete. Water (300 ml) was added to the mixture and the aqueous extracted with DCM (300 ml). The combined DCM layers were dried over $MgSO_4$ and concentrated in vacuo to give 18A. LCMS indicated a purity of 94.4%.

Intermediate 17B (2.08 g, 5.08 mmol, 1 equiv) was dissolved in DCM (25 ml), carbonyl diimidazole (1.15 g, 7.11 mmol, 1.4 equiv) was added at room temperature and the mixture was stirred overnight under nitrogen. LC analysis indicated the reaction was complete. Water (70 ml) was added to the mixture and the aqueous extracted with DCM (70 ml). The combined DCM layers were dried over $MgSO_4$ and concentrated in vacuo to give 18B (2.1 g, 95% yield). Chiral LC indicated an enantiomeric excess of 99.0%

Example 7

Synthesis of Intermediates 19A and 19B

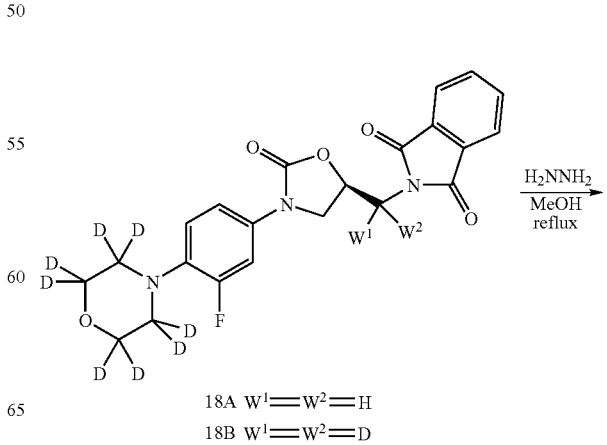

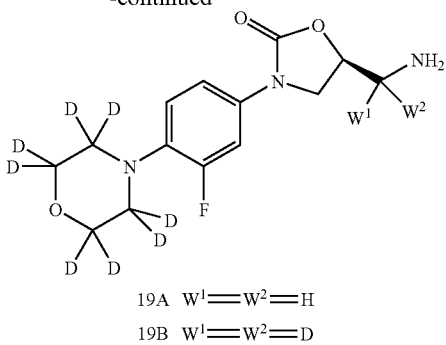

19A W¹═W²═H
19B W¹═W²═D

MeOH (100 ml) and hydrazine hydrate (6.1 ml, 0.125 mol, 5.5 equiv) were added to a flask containing 18A (9.9 g, 23 mmol, 1 equiv). The mixture was stirred at reflux temperature for 1 h. The reaction mixture was allowed to cool to room temperature, water (200 ml) was added, and the mixture was extracted with DCM (2×200 ml). The combined DCM extracts were washed with water (100 ml), dried over MgSO₄ and concentrated in vacuo to give 19A (6.0 g, 87% yield). LCMS indicated a purity of 96.8%.

MeOH (20 ml) and hydrazine hydrate (1.4 ml, 26.5 mmol, 5.5 equiv) were added to a flask containing 18B (2.1 g, 4.8 mmol, 1 equiv). The mixture was stirred at reflux temperature for 1 h. The reaction mixture was allowed to cool to room temperature, water (40 ml) was added, and the mixture was extracted with DCM (2×40 ml). The combined DCM extracts were washed with water (100 ml), dried over MgSO₄ and concentrated in vacuo to give 19B (1.26 g, 86% yield). Chiral LC indicated an enantiomeric excess of 99.3%.

Example 8

Synthesis of Intermediates 20A and 20B

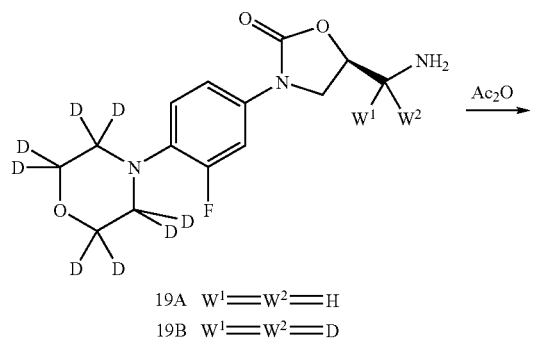

19A W¹═W²═H
19B W¹═W²═D

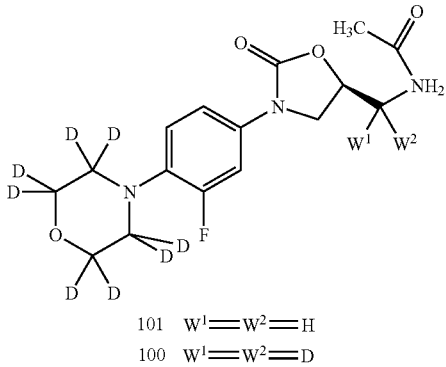

101 W¹═W²═H
100 W¹═W²═D

Intermediate 19A (6.0 g, 0.02 mol, 1 equiv) was stirred in toluene (90 ml) for 15 min. Acetic anhydride (5.4 ml, 0.057 mol, 2.9 equiv) was added dropwise at room temperature. The mixture was warmed to 35° C. with a water bath for 5 min to enhance the solubility of 19A. The reaction mixture was then stirred at room temperature for 1 h, was cooled to 0° C. and filtered to give compound 101 (5.3 g, 78% yield). LC indicated a purity of 99.1%. Chiral LC indicated an enantiomeric excess of 99.4%. ¹H-NMR (300 MHz, CDCl₃): δ 2.03 (s, 3H), 3.61-3.66 (m, 2H), 3.71-3.77 (m, 1H), 4.00 (apparent t, J=8.9, 1H), 4.71-4.79 (m, 1H), 6.50-6.54 (m, 1H), 6.88 (apparent t, J=8.9, 1H), 7.04 (dd, J₁=10.0, J₂=1.6, 1H), 7.41 (dd, J=14.6, J₂=2.7, 1H). HPLC (method: RP80A, 150 mm×4.6 mm column—gradient method 5-95% ACN+0.1% formic acid, with 5 min hold at 5% ACN prior to gradient, gradient over 10 mins, followed by 10 min hold at 95% ACN; T=30° C.; Wavelength: 258 nm): retention time: 11.45 min. Chiral HPLC (method: Chiralpak AD-H; 250×4.6 mm column; 5 μm particle size—hexane/IPA/DEA (80:20:01); T=40° C.; Wavelength: 258 nm): 11.80 min for desired enantiomer, 14.21 min for minor enantiomer; ee=99.8%. MS (M+H⁺): 346.5.

Intermediate 19B (1.25 g, 4.09 mmol, 1 equiv) was stirred in toluene (20 ml) for 15 min. Acetic anhydride (1.12 ml, 11.86 mol, 2.9 equiv) was added dropwise at room temperature. The mixture was warmed to 35° C. with a water bath for 5 min to enhance the solubility of 19B. The reaction mixture was then stirred at room temperature for 1 h, was cooled to 0° C. and filtered to give compound 100 (1.05 g, 74% yield). LC indicated a purity of 99.4%. Chiral LC indicated an enantiomeric excess of 98.9%. ¹H-NMR (300 MHz, CDCl₃): δ 2.00 (s, 3H), 3.74 (dd, J₁=9.1, J₂=6.8, 1H), 4.00 (t, J=9.1, 1H), 4.75 (dd, J₁=8.8, J₂=6.8, 1H), 6.52 (bs, 1H), 6.88 (t, J=8.8, 1H), 7.02-7.06 (m, 1H), 7.41 (dd, J₁=4.5, J₂=2.6, 1H). HPLC (method: RP80A, 150 mm×4.6 mm column—gradient method 5-95% ACN+0.1% formic acid, with 5 min hold at 5% ACN prior to gradient, gradient over 10 mins, followed by 10 min hold at 95% ACN; T=30° C.; Wavelength: 258 nm): retention time: 11.55 min. Chiral HPLC (method: Chiralpak AD-H; 250×4.6 mm column; 5 μm particle size—hexane/IPA/DEA (80:20:01); T=40° C.; Wavelength: 258 nm): 10.63 min for desired enantiomer, 13.18 min for minor enantiomer; ee=98.9%. MS (M+H⁺): 348.3.

Example 9

Synthesis of 2,2,6,6-d₄-morpholine (33) and perdeuteromorpholine (10)

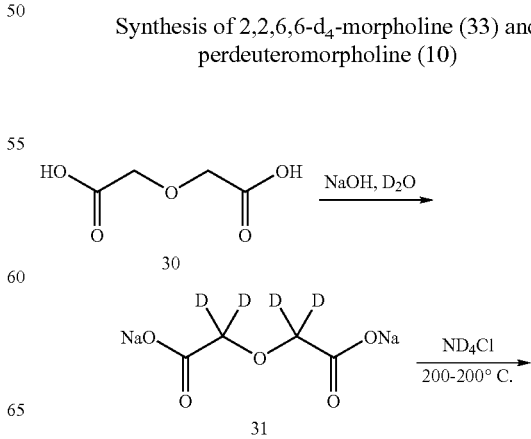

31
-continued

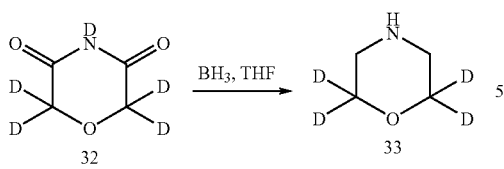

Diglycolic acid (30) is treated with sodium hydroxide in $D_2O$ to produce the corresponding deuterated disodium compound 31. Compound 31 is then heated in the presence of perdeuteroammonium chloride to produce the $d_4$-dioxomorpholine 32, which is then reduced by boron trihydride in THF to produce the desired 2,2,6,6-$d_4$-morpholine (33). The tetradueteromorpholine 33 can be used in place of perdeuteromorpholine 10 in Example 1, above, to produce compounds of formulae I and Ia wherein each Z is deuterium and each Y is hydrogen, such as compounds 102 and 103.

Example 10

Synthesis of Compound 103

32
-continued

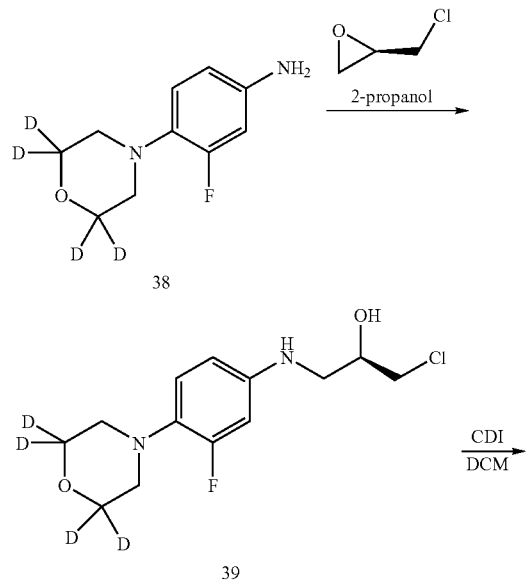

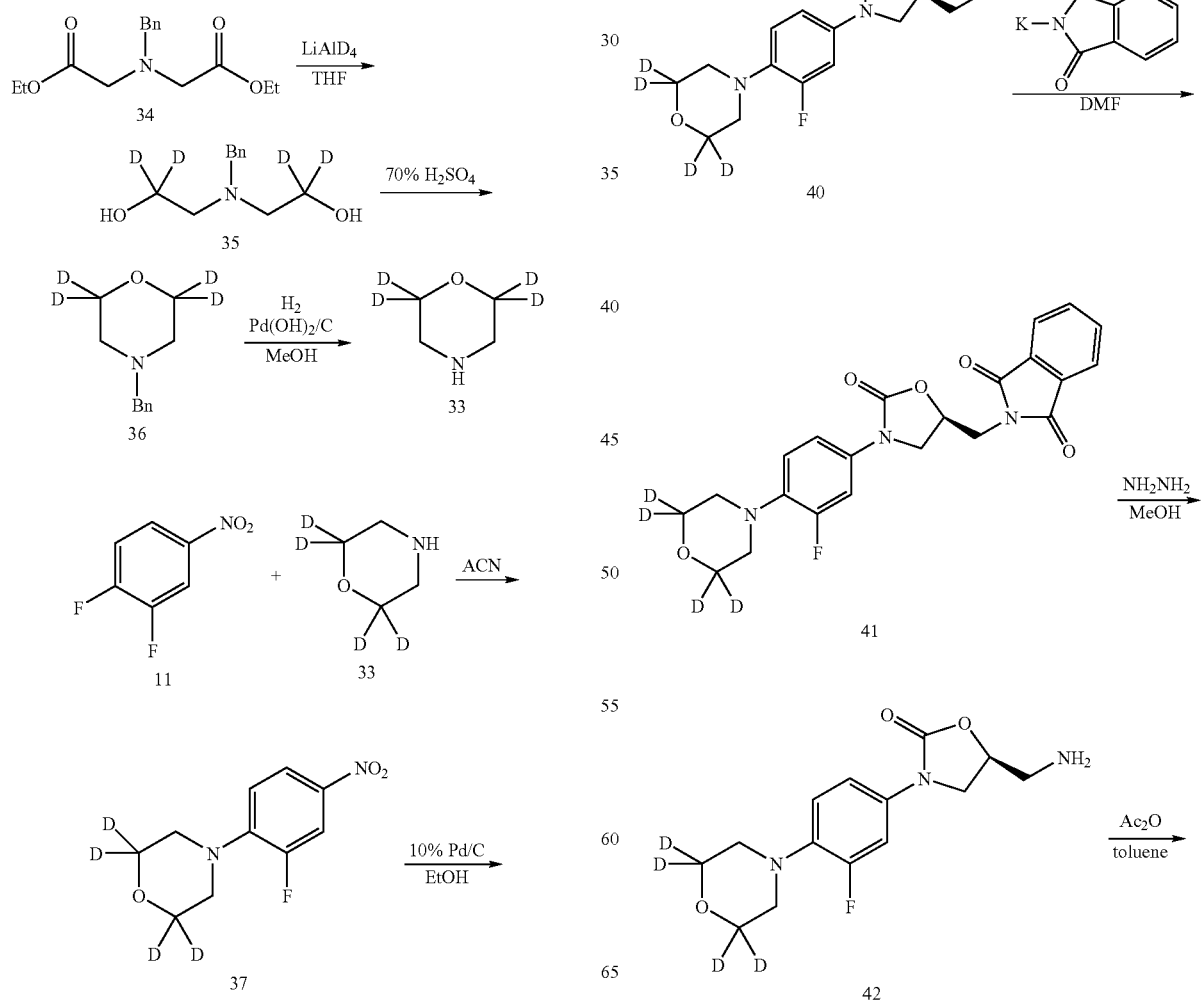

-continued

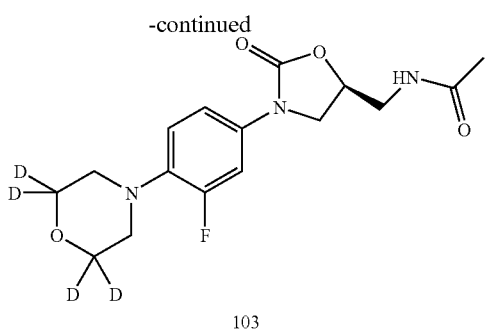

103

N-benzyl 2,2'-iminobis-ethan-1,1-d2-ol (35) To a solution of diethyl benzyliminodiacetate (34, 55.0 g, 196.9 mmol) in anhydrous tetrahydrofuran (500 mL) at 0° C. was added lithium aluminum deuteride (16.5 g, 393.8 mmol, Cambridge Isotopes, 98 atom % D) in portions with internal temperature below 10° C. After addition the reaction was stirred overnight at room temperature and then quenched sequentially with water (16.5 mL), 15 wt % sodium hydroxide (16.5 mL), and water (49.5 mL) at 0° C. The suspension was stirred 2 hours at room temperature, filtered over celite cake, and washed with THF (400 mL). The filtrate was evaporated in vacuo to give 35 (36.5 g, 93%) as a pale yellow oil.

N-benzylmorpholine-2,2,6,6-$d_4$ (36) A solution of 35 (36.5 g, 183.4 mmol) in 70% sulfuric acid (138 mL) was heated in a sealed tube at 150° C. for 16 hours, cooled to room temperature, and slowly poured onto crushed ice (300 g). The resulting mixture was slowly basified to pH 9 with solid potassium carbonate and mixed with EtOAc (500 mL). The suspension was filtered over a celite cake and washed with EtOAc (400 mL). For the filtrate the two layers were split and the aqueous layer was extracted with EtOAc (2×300 mL). The combined organic layers were dried over sodium sulfate and evaporated in vacuo to give N-benzylmorpholine-2,2,6,6-$d_4$ (compound 36) (31.6 g, 95%) as lightly tan oil. The signal corresponding to the protons alpha to the oxygen is not visible in the $^1$H NMR spectrum.

Morpholine-2,2,6,6-$d_4$ (33) A solution of N-benzylmorpholine-2,2,6,6-$d_4$ (36) (31.6 g) in methanol (300 mL) was shaken under hydrogen (30 psi) with Pd(OH)$_2$ on carbon (6.3 g) as catalyst until no further hydrogen was consumed. The reaction mixture was filtered over a celite cake and washed with methanol (400 mL). The filtrate was evaporated at 25° C. to give morpholine-2,2,6,6-$d_4$ (33) as a pale yellow oil in quantitative yield. The signal corresponding to the protons alpha to the oxygen is not visible in the $^1$H NMR spectrum.

4-(2-fluoro-4-nitrophenyl)morpholine-2,2,6,6-$d_4$ (37) To a solution of 3,4-difluoronitrobenzene (11, 26.5 g, 166.3 mmol) and diisopropylethylamine (76 mL, 436.5 mmol) in acetonitrile (350 mL) was added compound 33 (174.6 mmol). The reaction was refluxed for 16 hours and then the volatiles were removed. The crude residue was taken up with water (300 mL). The precipitate was filtered, washed with water (200 mL) and heptane (300 mL), and dried under vacuum at 40° C. for 5 hours to give 37 (34.8 g, 91%) as a bright yellow solid.

3-fluoro-4-(morpholino-2,2,6,6-$d_4$)-aniline (38) A solution of 37 (34.8 g) in ethanol (400 mL) was shaken under hydrogen (30 psi) with 10 wt % Pd/C (7.0 g, containing 50 wt % water) until no hydrogen was consumed (ca. 3 hours). The reaction mixture was filtered over celite and washed with ethanol (400 mL). The filtrate was evaporated in vacuo to give 38 (26.7 g, 85%) as a white solid.

(R)-1-chloro-3-(3-fluoro-4-(morpholino-2,2,6,6-$d_4$)-phenylamino)propan-2-ol (39) To a solution of 38 (2.36 g, 11.8 mmol) in 2-propanol (30 mL) was added (R)-(−)-epichlorohydrin (1.2 g, 13.0 mmol). The reaction was refluxed for 15 hours and another 0.24 g (2.6 mmol) of (R)-(−)-epichlorohydrin was added. The reaction was refluxed another 6 hours and the solvent was removed to give 39 as an oil that was used for the next step without further purification.

(R)-5-(chloromethyl)-3-(3-fluoro-4-(morpholino-2,2,6,6-$d_4$)-phenyl)oxazolidin-2-one (40) A solution of 39 (ca. 11.8 mmol) and 1,1'-carbonyldiimidazole (2.68 g, 16.5 mmol) in dichloromethane (100 mL) was stirred overnight at room temperature and evaporated to give a crude oil containing 40.

(S)-2-((3-(3-fluoro-4-(morpholino-2,2,6,6-$d_4$)-phenyl)-2-oxooxazolidin-5-yl)methyl)isoindoline-1,3-dione (41) To a solution of 40 (ca. 11.8 mmol) in DMF (50 ml) was added phthalimide potassium salt (2.84 g, 15.3 mmol). The reaction mixture was heated at 100° C. for 6 hours, cooled to room temperature, taken up with water (100 mL), and extracted with MTBE (3×100 mL). The combined organic layers were washed with brine (2×200 mL), dried with sodium sulfate, and evaporated in vacuo. The crude solid was triturated with MTBE (100 mL) to give 41 (3.3 g, 66% for 3 steps) as a white solid.

(S)-5-(aminomethyl)-3-(3-fluoro-4-(morpholino-2,2,6,6-$d_4$)-phenyl)oxazolidin-2-one (42) A solution of 41 (3.3 g, 7.68 mmol) and hydrazine monohydrate (2.07 g, 42.3 mmol) in methanol (40 mL) was refluxed for 1 hour. The reaction mixture was evaporated in vacuo, taken up with water (100 mL), and extracted with dichloromethane (3×100 mL). The combine organic layers were washed with water (150 mL), dried over sodium sulfate, and evaporated in vacuo to give 9 (2.16 g) as a tan oil in quantitative yield.

(S)—N-((3-(3-fluoro-4-(4-morpholino-2,2,6,6-$d_4$)-phenyl)-2-oxooxazolidin-5-yl)methyl)acetamide (103) To a solution of 42 (2.16 g, 7.22 mmol) in toluene at room temperature was added acetic anhydride (2 mL, 20.9 mmol). The reaction mixture was warmed at 35° C. for 5 min and then stirred overnight at ambient temperature. The reaction mixture was cooled to 0° C., filtered, washed with toluene, and dried at 40° C. for 4 hours to give 103 (1.2 g, 49%) as a white solid. The signal corresponding to the protons alpha to the oxygen is not visible in the $^1$H NMR spectrum.

Example 11

Antimicrobial activity was tested in vivo using the Murine Assay procedure. Groups of female mice (six mice of 18-20 grams each) are injected intraperitoneally with *Staphylococcus aureus* bacteria which are thawed just prior to use and suspended in brain heart infusion with 4% brewers yeast (*Staphylococcus aureus*) or brain heart infusion (*Streptococcus* species). Antibiotic treatment at six dose levels per drug is administered one hour and five hours after infection by either oral intubation or subcutaneous routes. Survival was observed daily for six days. ED$_{50}$ values based on mortality ratios are calculated using probit analysis. The subject compounds are compared against a control (e.g., vancomycin).

Example 12

The in vitro activity experiments are conducted by standard dilution methods known to those skilled in the art. Briefly, serial two-fold dilutions of antibiotic are prepared in a diluent, and a standard volume of mycobacterial growth medium is added to drug aliquot. The medium is inoculated with a standardized mycobacterial cell suspension, and then incubated under appropriate conditions. Following incubation, the Minimal Inhibitory Concentration (MIC) is determined by visual observation. The MIC is defined as the lowest drug concentration (in μg/ml) required to inhibit mycobacterial growth.

Example 13

In vivo data is obtained from CD-1 mice infected intravenously with $1\times10^7$ viable *M. tuberculosis* (Erdman strain). Twenty-four hours later drug treatment is initiated. All the drugs are given by oral gavage twice daily for four weeks. At the end of therapy, viable cell counts are determined from homogenates of spleens and lungs.

Example 14

In Vitro Antibacterial Activities

The in vitro antibacterial activity of linezolid, compounds 100 and 101 and six comparator agents was determined for a battery of Gram-positive and -negative bacteria.
Materials and Methods The three test compounds were stored at 4° C. until tested. Six comparator agents were also tested including vancomycin (Sigma-Aldrich, Catalog #V2002), linezolid (Chem Pacific), oxacillin (Fluka, Catalog #28221), amoxicillin (Sigma, Catalog #A-8523)/clavulanate (Sigma, Catalog #P3494), daptomycin (Cubist) and levofloxacin (Fluka, Catalog #28266).

All test articles and drugs were dissolved in 50% dimethyl sulfoxide (DMSO) at one-half the volume needed to prepare the stock solution. Once the compound was in solution, the rest of the volume was added as sterile deionized water. The drug solutions were allowed to stand at room temperature for 1 hr to allow for auto-sterilization. Stock solutions were prepared at 40-fold the highest final test concentration in the test plate. The final concentration of DMSO in the assay was 2.5%.
Test Organisms The test organisms were obtained from clinical laboratories; quality control cultures were from the American Type Culture Collection. The test groups included *Staphylococcus aureus*, *Staphylococcus epidermidis*, *Enterococcus faecalis*, *Enterococcus faecium*, *Streptococcus pneumoniae*, *Streptococcus pyogenes*, *Streptococcus agalactiae*, *Haemophilus influenzae*, and *Moraxella catarrhalis*. Various phenotypic susceptibility/resistance groups were represented. Organisms received were streaked for isolation on agar medium appropriate to each organism. Colonies were picked by swab from the isolation plates and put into suspension in the appropriate media containing a cryoprotectant. The suspensions were aliquoted into cryogenic vials and maintained at −80° C. The isolates were thawed and passaged on the appropriate agar medium: Trypticase Soy agar (TSA) for most organisms, TSA plus 5% sheep blood for streptococci, and chocolate agar for *Haemophilus*. The plates were incubated overnight at 35° C. *Haemophilus* plates were incubated in the presence of $CO_2$.
Test Media The medium employed for the MIC assay was Mueller Hinton II Broth (MHB II-Becton Dickinson, Sparks, Md. #212322, Lot #7143673) for most of the organisms. MHB II was supplemented with 2% lysed horse blood (Cleveland Scientific Lot #H93152) to accommodate the growth of *Streptococcus pneumoniae*. *Haemophilus influenzae* was tested in *Haemophilus* Test Medium. On the day of the test, the medium to be used in the daptomycin row of the daughters was supplemented with calcium ions to the final concentration of 50 μg/mL, taking into account the calcium that was already present in the medium. All media were prepared at 105% normal weight to offset the DMSO:water (5 μL drug solution) in the final microdilution panels. The amounts of supplements added to the medium were also calculated at 105%.
Test Procedure The MIC assay method followed the procedure described by the Clinical and Laboratory Standards Institute and employed automated liquid handlers to conduct serial dilutions and liquid transfers. Automated liquid handlers included the Multidrop 384, Labsystems, Helsinki, Finland; Biomek 2000 and Multimek 96, Beckman Coulter, Fullerton Calif. The wells of standard 96-well microdilution plates (Falcon 3918) were filled with 150 μL of DMSO:deionized $H_2O$ (1:1) on the Multidrop 384. The drugs were dispensed into Column 1 of a deep well plate. The Biomek 2000 transferred 150 μL of each drug into one well in Column 1 of a "mother plate" and completed serial transfers through Column 11 in the mother plates. The wells of Column 12 contained no drug and were the organism growth control wells.

The daughter plates were loaded with 85 μL of the appropriate test media described above using the Multidrop 384. The daughter plates were prepared on the Multimek 96 instrument which transferred 5 μL of drug solution from each well of a mother plate to each corresponding well of each daughter plate in a single step.

Standardized inoculum of each organism was prepared per CLSI methods (Clinical and Laboratory Standards Institute. Methods for Dilution Antimicrobial Susceptibility Tests for Bacteria That Grow Aerobically; Approved Standard—Seventh Edition. Clinical and Laboratory Standards Institute document M7-A7 [ISBN 1-56238-587-9]. Clinical and Laboratory Standards Institute, 940 West Valley Road, Suite 1400, Wayne, Pa. 19087-1898 USA, 2006). Suspensions were prepared in MHB to equal a 0.5 McFarland standard. The suspensions were diluted 1:19 in broth appropriate to the organism. The inoculum for each organism was dispensed into sterile reservoirs divided by length (Beckman Coulter), and the Biomek 2000 was used to inoculate the plates. Daughter plates were placed on the Biomek 2000 work surface reversed so that inoculation took place from low to high drug concentration. The Biomek 2000 delivered 10 μL of standardized inoculum into each well.

This yielded a final cell concentration in the daughter plates of approximately $5\times10^5$ colony-forming units/mL. Thus, the wells of the daughter plates ultimately contained 85 μL of broth, 5 μL of drug solution, and 10 μL of bacterial inoculum. Plates were stacked 3 high, covered with a lid on the top plate, placed in plastic bags, and incubated at 35° C. for approximately 18 hours for most of the isolates. The *Streptococcus* and *Haemophilus* plates were read after 20 hours of incubation. The microplates were viewed from the bottom using a plate viewer. For each of the test media, an un-inoculated solubility control plate was observed for evidence of drug precipitation. The MIC was read and recorded as the lowest concentration of drug that inhibited visible growth of the organism.
Results and Discussion $MIC_{90}$ values for compounds 100 and 101 against both methicillininsensitive *S. aureus* (MSSA) and methicillin-resistant *S. aureus* (MRSA) were 4 μg/ml, the same as linezolid. Compounds 100 and 101 and linezolid all gave $MIC_{90}$ values of 2 μg/ml for the following groups of organisms: community-acquired MRSA, methicillin-sensitive *S. epidermidis*

(MSSE), methicillin-resistant *S. epidermidis* (MRSE), vancomycin-sensitive *E. faecalis*, vancomycin-resistant *E. faecalis*, and vancomycin-resistant *E. faecium*. For vancomycin-sensitive *E. faecium*, compounds 100 and 101, and linezolid all produced a value of 2 μg/ml.

Susceptibility testing of 27 penicillin-sensitive *S. pneumoniae*, 27 penicillin-intermediate *S. pneumoniae*, and 28 penicillin-resistant *S. pneumoniae* revealed identical $MIC_{90}$ values of 2 μg/ml for compounds 100 and 101 and linezolid. The potency of compounds 100 and 101 against *S. pyogenes* was also identical to that of linezolid (1 μg/ml). For *S. agalactiae*, the $MIC_{90}$ value of compounds 100 and 101 was identical to that of linezolid (2 μg/ml). As expected, linezolid exhibited poor activity against *H. influenzae*, as did compounds 100 and 101. The $MIC_{90}$ value of 4 μg/ml obtained for 30 *M. catarrhalis* isolates was shared by all compounds 100 and 101, while linezolid produced a value of 8 μg/ml.

All drugs were soluble at the concentrations tested in all three media. Susceptibility values fell within CLSI-approved ranges for the quality control cultures and antibiotics tested (Clinical and Laboratory Standards Institute. Performance Standards for Antimicrobial Susceptibility Testing; Sixteenth Informational Supplement. CLSI document M100-S16 [ISBN 1-56238-588-7].

Clinical and Laboratory Standards Institute, 940 West Valley Road, Suite 1400, Wayne, Pa.

19087-1898 USA, 2006).

Figure 5:
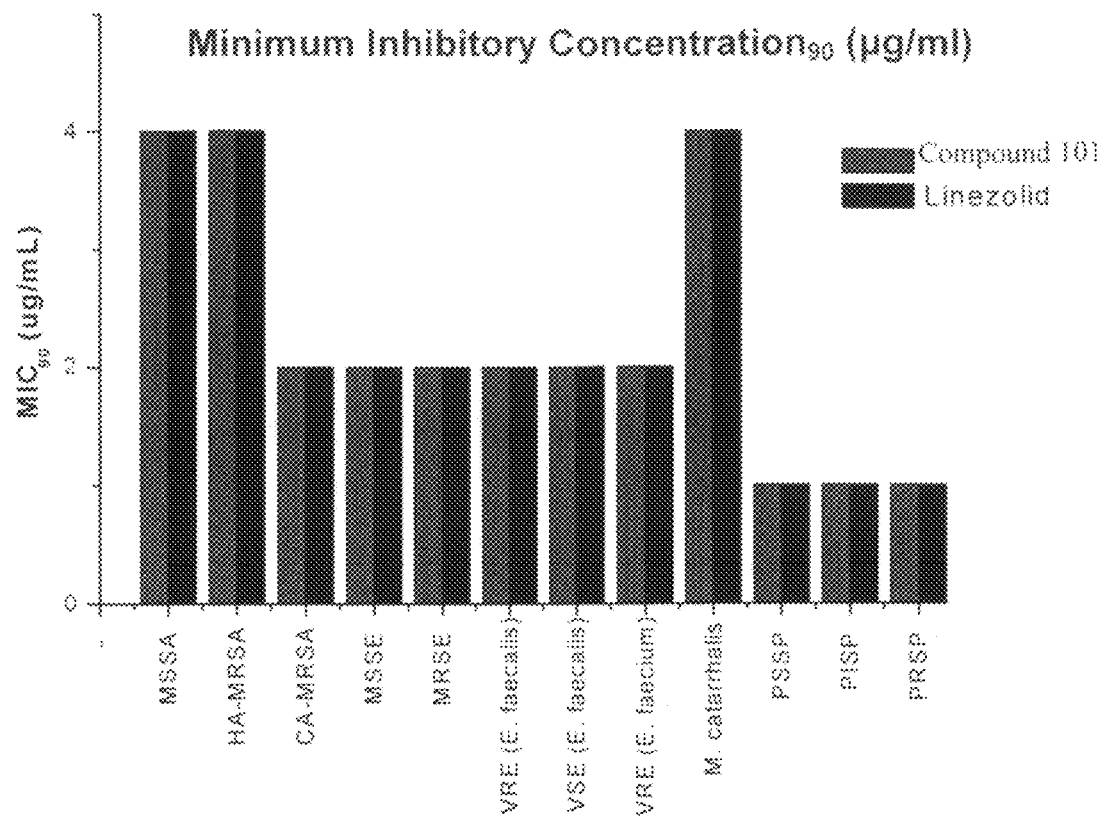
FIG. 5 depicts antimicrobial activity of compound 101 compared to that of linezolid.
Figure 6A:
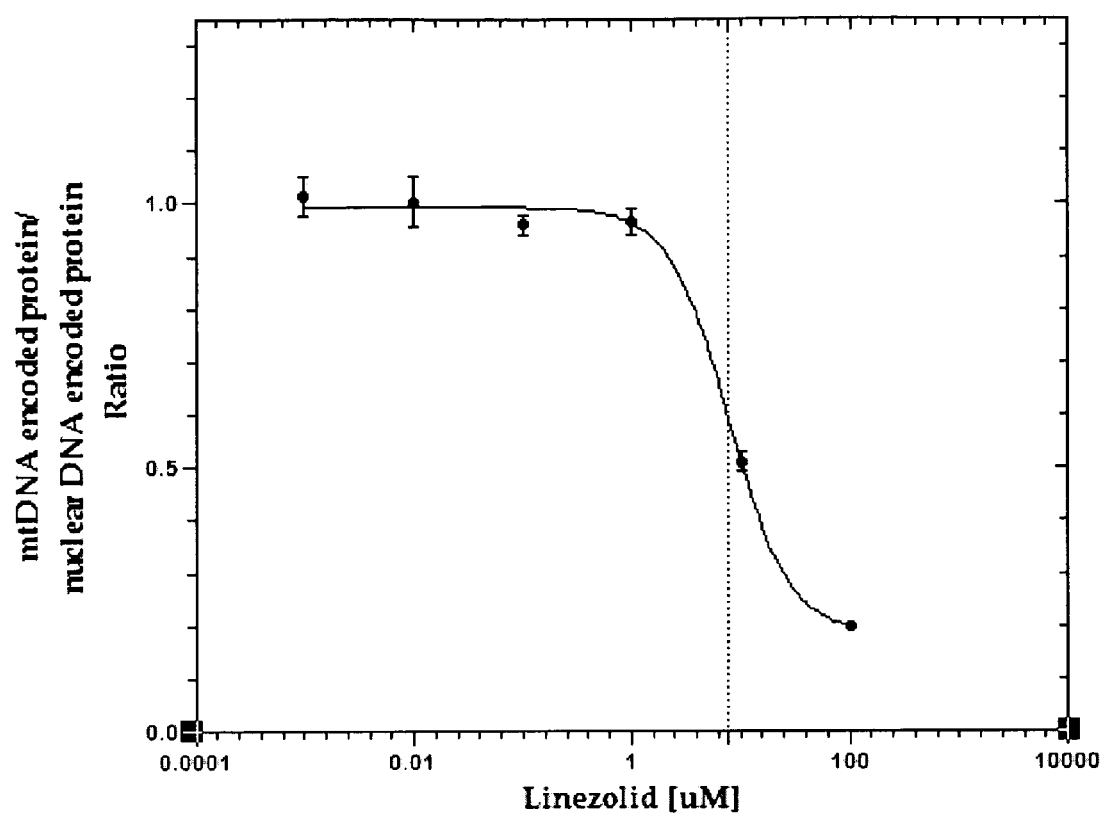
FIG. 6 depicts inhibition of mtDNA-encoded protein synthesis by linezolid (6A), compound 100 (6B), compound 101 (6C), and compound 103 (6D). The ratio of mtDNA encoded protein over nuclear DNA encoded protein was plotted against the concentration of tested compounds.
Figure 6B:
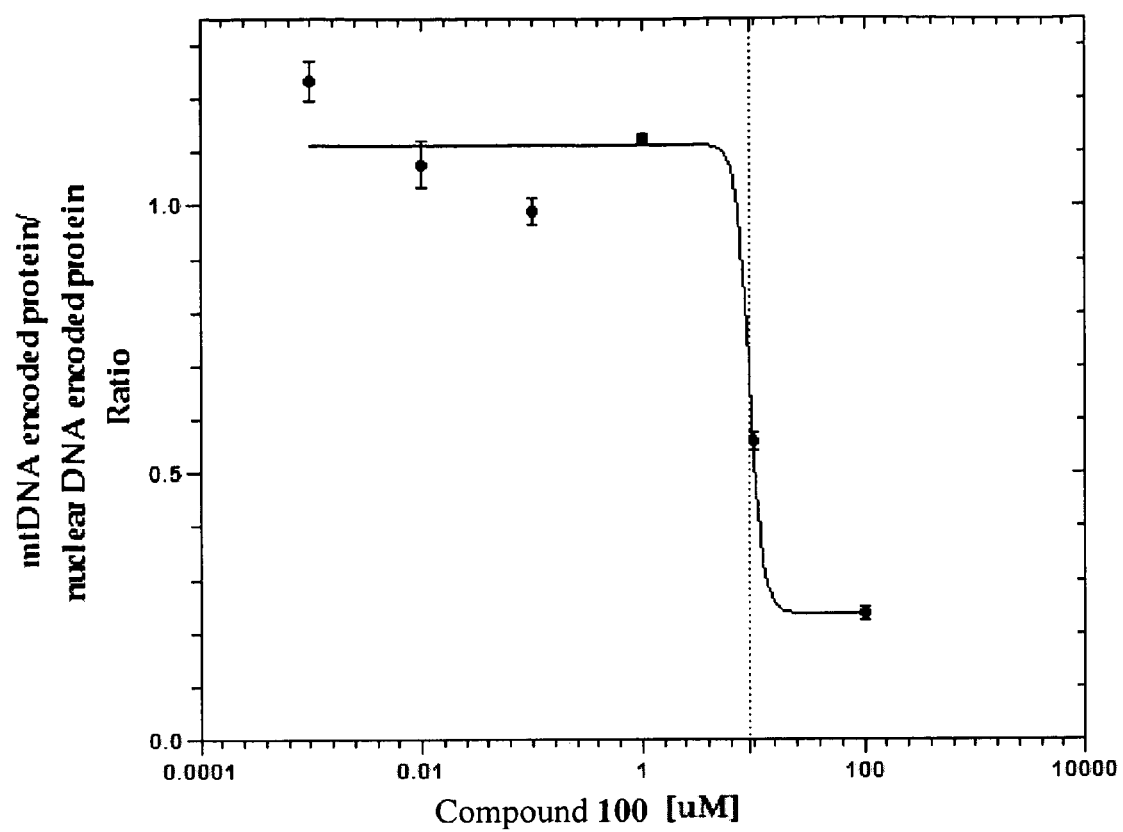
Figure 6C:
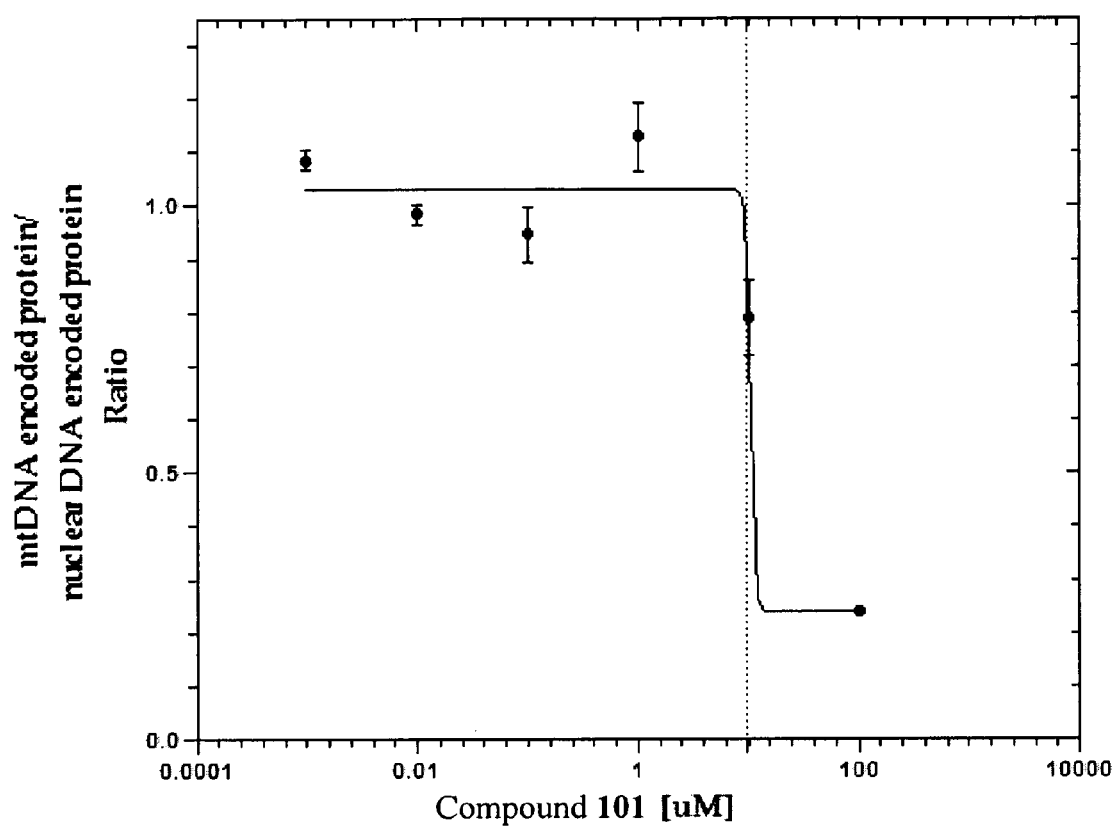
Figure 6D:
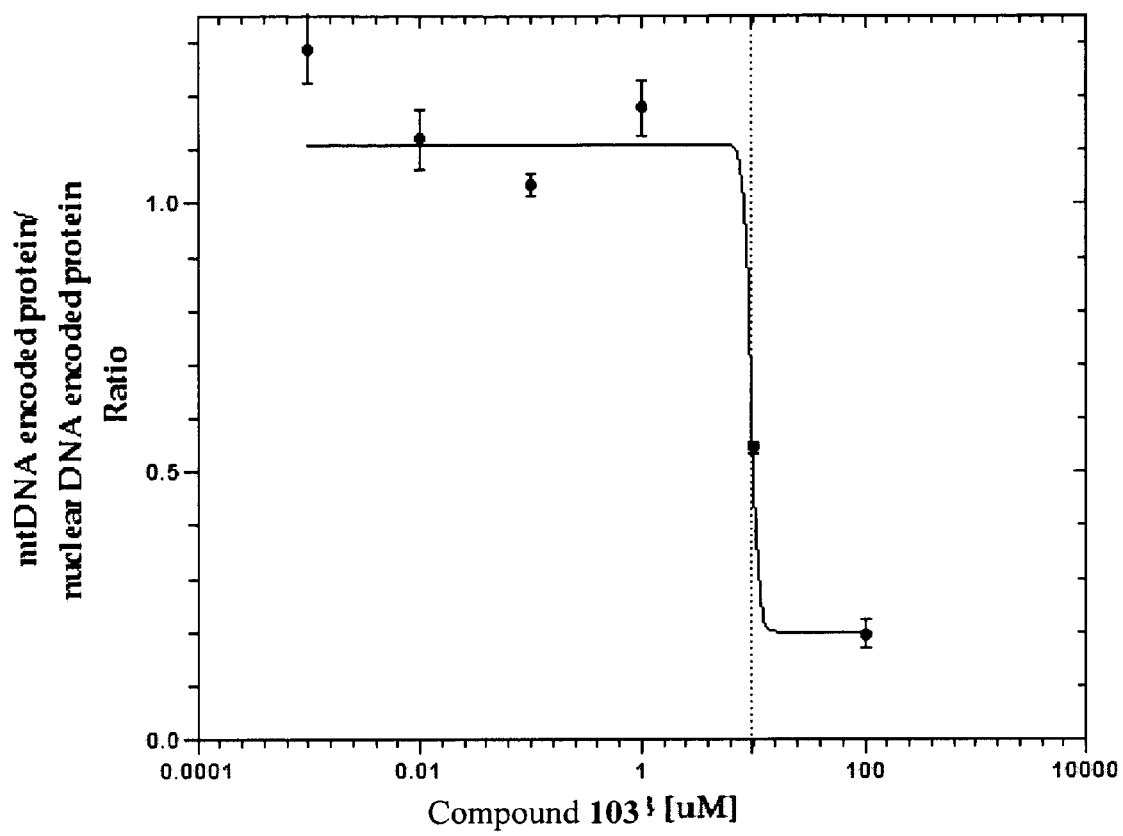

In conclusion, compounds 100 and 101 exhibited good activity against antibiotic resistant Grampositive pathogens including MRSA, VRE, and PRSP. The profile of these compounds was similar to that of linezolid. FIG. 5 shows $MIC_{90}$ data for compound 100 compared with that of linezolid.

Example 15

Mitochondria Toxicity Study

HepG2 cells were seeded at 50,000 cells per well in 6-well plates and grown in High-Glucose DMEM in the presence of 6 different concentrations of compound (100 μM, 10 μM, 1 μM, 100 nM, 10 nM and 1 nM). Each concentration was tested in triplicate. Cells were also grown in the corresponding DMSO concentrations present in each of the treatments ($5 \times 10^{-1}$%, $5 \times 10^{-2}$%, $5 \times 10^{-3}$%, $5 \times 10^{-4}$%, $5 \times 10^{-5}$%, $5 \times 10^{-6}$%).

The medium with the compound was changed after 72 hours of treatment and kept for further analysis.

When the cells reached an average of 4 population doublings in the compound, they were trypsinized, centrifuged and washed with phosphate buffered saline. The cells were solubilized in 1.5% laurylmaltoside (in 25 mM Hepes, 100 mM NaCl, pH 7.4), centrifuged at 25,000 g for 20 minutes and supernatants kept for assay.

Enzyme quantity from each well was assessed with duplicate dipsticks. Each dipstick was loaded with 2 μg of solubilized protein to determine the levels of Complex IV (a mtDNA-encoded protein), and Frataxin (a nuclear DNA-encoded protein). Extracts were then stored at −80° C. for further analysis.

The amount of enzymes captured on the dipstick was determined quantitatively with a Hamamatsu Immunochromato Reader. The absorbance signal of two dipsticks measuring enzyme quantity from the same well was averaged (CV<1%) and the means for each triplicate treatment were normalized by interpolation against an assay specific calibration curve.

Complex IV/Frataxin Ratios were determined for each triplicate treatment from interpolated values. Triplicate ratios for each treatment concentration were analyzed using a non-linear regression curve in Graph Pad (Log[inhibitor] vs. response—variable slope). Results are shown in FIGS. 6A-6D. $IC_{50}$ data are listed in Table 1.

TABLE 1

| $IC_{50}$ values for compounds 100 and 101 and linezolid | |
|---|---|
| Compound | $IC_{50}$ (μM) |
| Linezolid | 7.8 |
| Compound 100 | 9.3 |
| Compound 101 | 10.5 |
| Compound 103 | 9.7 |

In conclusion, the mitochondria toxicity for compounds 100, 101 and 103 is comparable to that of linezolid.

Example 16

Pharmacokinetic Study in Rats

Materials and Methods 18.08 mg of linezolid, 10.00 mg of compound 101 and 10.01 mg of compound 103 were dissolved in 10% DMI, 15% Ethanol, 35% PG, and 40% D5W independently to yield a final concentration at 10 mg/mL (pH ~6). The combo dose was prepared by mixing both by 1:1 to yield a concentration of 5 mg/mL for each compound (pH ~6) for intravenous and oral administration. The obtained solution was clear and colourless. The concentrations of linezolid, compounds 101 and 103 in each individual dose were confirmed by HPLC method.

Male Sprague Dawley rats (body weight: 170 g to 220 g) were used in this study. Before the pharmacokinetic studies, animals were randomly assigned to the treatment groups. The treatment schedules are shown in Table 2.

TABLE 2

Experimental Design

| No. of Male Rats | Test Article | Test Article Formulation | Dose Route | Target Dose Level (mg/kg) | Target Dose Concentration (mg/mL) | Target Dose Volume (mL/kg) |
|---|---|---|---|---|---|---|
| 3 | linezolid + compound 101 | 10% DMI/15% Ethanol/35% PG/ 40% D5W | IV | 5 mg/kg for each | 5 mg/mL for each | 1 |
| 3 | linezolid + compound 101 | 10% DMI/15% Ethanol/35% PG/ 40% D5W | PO | 5 mg/kg for each | 5 mg/mL for each | 1 |

TABLE 2-continued

Experimental Design

| No. of Male Rats | Test Article | Test Article Formulation | Dose Route | Target Dose Level (mg/kg) | Target Dose Concentration (mg/mL) | Target Dose Volume (mL/kg) |
|---|---|---|---|---|---|---|
| 3 | linezolid + compound 103 | 10% DMI/15% Ethanol/35% PG/ 40% D5W | IV | 5 mg/kg for each | 5 mg/mL for each | 1 |
| 3 | linezolid + compound 103 | 10% DMI/15% Ethanol/35% PG/ 40% D5W | PO | 5 mg/kg for each | 5 mg/mL for each | 1 |

Blood samples were collected by retro-orbital at 0 (pre-dose) and 0.083, 0.25, 0.5, 1, 2, 4, 6, 8, 10, 12, and 24 hours post-dose. The plasma samples and the dose formulation were stored at −20° C. until bioanalysis.

Sample Analysis

The concentrations of linezolid, compounds 101 and 103 in plasma were determined using a high performance liquid chromatography/mass spectrometry (HPLC/MS/MS) method.

LC-MS/MS Apparatus

The LC system comprised an Agilent (Agilent Technologies Inc. USA) liquid chromatograph equipped with an isocratic pump (1100 series), an autosampler (1100 series) and a degasser (1100 series). Mass spectrometric analysis was performed using an API3000 (triple-quadrupole) instrument from AB Inc (Canada) with an ESI interface. The data acquisition and control system were created using Analyst 1.4 software from ABI Inc.

Other equipment: XW-80A Vortex mixer (Shanghai); TGL-16B high speed centrifuge (Shanghai), Millipore Academic Ultrapure-water generating system.

Internal Standard (Quetiapine) was a gift from Shanghai Institute of Pharmaceutical Industry. Acetonitrile and methanol (Tedia Inc, USA) were HPLC grade. All other solvents and chemicals were analytical grade or better.

LC-MS/MS Conditions
Chromatographic Conditions
Column: Phenomenex Gemini, C6-pheny, 5 μm, (50 mm×4.6 mm)
Mobile phase: 0.1% Formic acid: Methanol=10:90
Elution rate: 1000 μL/min
Column temperature: 25° C.
Injection volume: 5 μL
Mass
Scan type: Positive MRM
Ion source: Turbo spray Ionization model: ESI
Nebulize gas: 8 L/min Curtain gas: 8 L/min Collision gas: 4 L/min
Ionspray voltage: 4500 v; Temperature: 450° C.
Other Parameters:

Preparation of Standard Stock Solution

A stock solution of linezolid, compounds 101 and 103 was prepared by dissolving the drug in methanol to yield a final concentration of 200 μg/mL, respectively. Then proper volume of these two solutions were transferred into one flask, and diluted to the mark with methanol to make a mixture of two compounds with the same concentration of 25 μg/mL. An aliquot of this mixture was diluted using methanol to get a series of working solutions of 25, 50, 250, 500, 2500, 5000, and 25000 ng/mL. Seven calibration standard samples containing 5000, 1000, 500, 100, 50, 10, and 5 ng/mL were obtained by adding 20 μL working solution prepared above into seven Eppendorff tubes containing 100 μL blank plasma. QC samples were prepared by spiking 100 μL blank plasma with 20 μL working solutions of 20000, 4000, and 40 ng/mL to yield final concentration of 4000, 800, and 8 ng/mL.

Stock solution of Quetiapine (internal standard, IS) was prepared by dissolving the drug in methanol to a final concentration of 200 μg/mL. This solution was diluted with methanol to yield a final concentration of 50 ng/mL.

Plasma Sample Process

Plasma samples (0.1 mL) were transferred to Eppendorff tube, then 20 μL methanol, and 300 μL IS solution (50 ng/mL) were added to it. After Vortexing for 1 min and centrifuging for 5 min at 15,000 rpm, 5 μL of supernatant was injected into LC/MS/MS.

Method Validation Results
Specificity

The chromatographic conditions showed that the blank plasma had no interference to the determination of linezolid, compounds 101 and 103, and IS.

Calibration Curve

The analytical curves were constructed using seven non-zero standards ranging from 5 to 5000 ng/mL. A blank sample (matrix sample processed without internal standard) was used to exclude contamination. The linear regression analysis of linezolid and compounds 101 and 103 were performed by plotting the peak area ratio (y) against the concentration (x) in ng/mL for linezolid, compounds 101 and 103, respectively. The linearity of the relationship between peak area ratio and

| Drug name | Q1 | Q3 | Dell time | DP (v) | FP (v) | EP (v) | CE (v) | CXP (v) |
|---|---|---|---|---|---|---|---|---|
| linezolid | 338.07 | 296.27 | 200 ms | 61 | 160 | 10 | 27 | 20 |
| compound 101 | 346.15 | 203.00 | 200 ms | 56 | 160 | 10 | 33 | 14 |
| compound 103 | 342.17 | 300.19 | 200 ms | 56 | 170 | 10 | 27 | 20 |
| Quetiapine | 384.2 | 253.2 | 200 ms | 50 | 200 | 10 | 31 | 15 | concentration were demonstrated by the correlation coefficients (R) obtained for the linear regressions of linezolid and compounds 101 and 103.

Intra-Assay Accuracy

The intra-assay accuracy results (ranged from 83.54% to 106.38% for linezolid, 90.51% to 115.21% for compound 101 and 94.00% to 113.32% for compound 103) showed that the method is reliable.

Data Analysis

Pharmacokinetic Data Analysis

The concentrations in plasma below the limit of quantitation (LOQ=5 ng/mL) were designated as zero. The pharmacokinetic data analysis was performed using noncompartmental analysis modules in WinNonlin2.0. The bioavailability was calculated as F (%)=(Dose$_{iv}$× AUC$_{oral(0-\infty)}$)/(Dose$_{oral}$×AUC$_{iv(0-\infty)}$)*100%.

Results and Discussion

Pharmacokinetics of Linezolid after Combinatory Administration

Figure 7A:
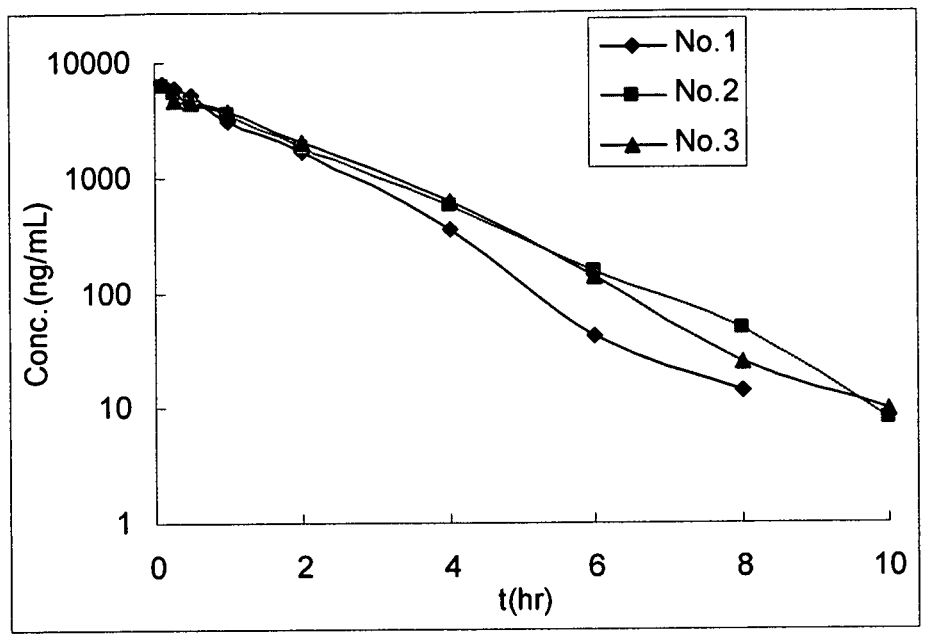
FIGS. 7A-7C depict concentration-time curve of linezolid in male rats following intravenous and oral administration of linezolid in combination with compound 101.
Figure 7B:
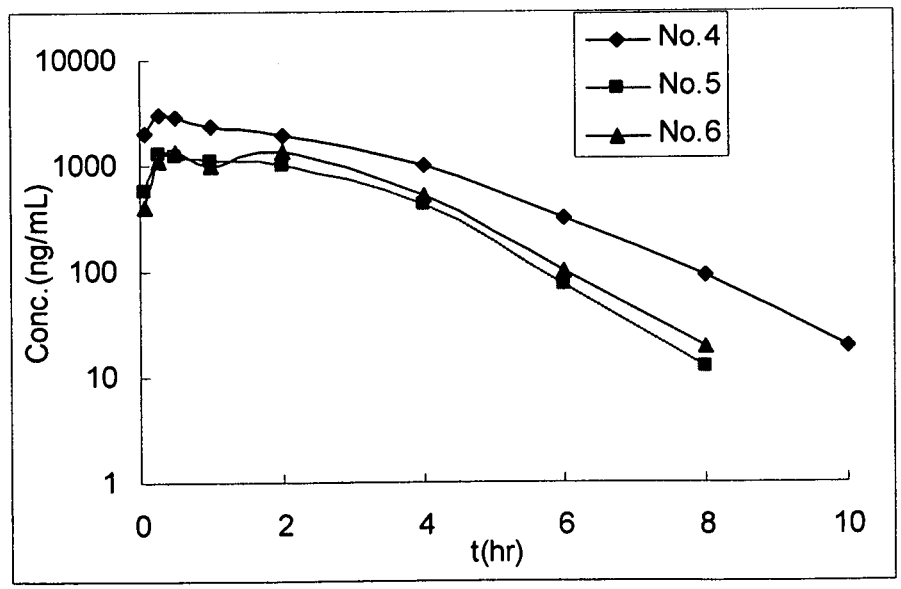
Figure 7C:
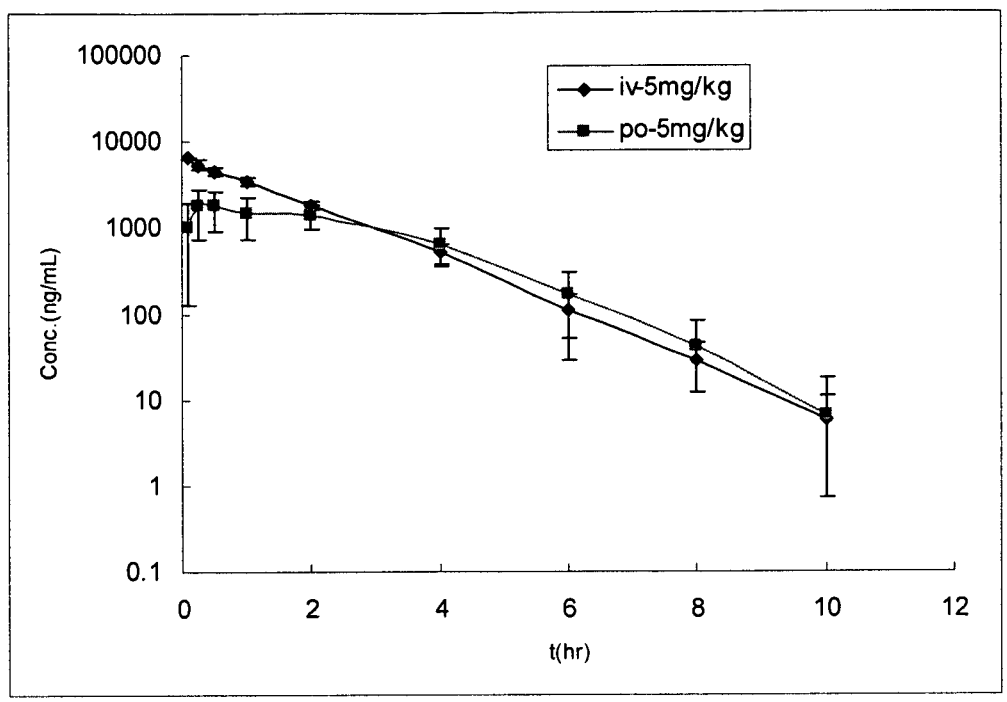

The individual and average concentration-time data of linezolid following intravenous and oral administration in combination with compound 101 are listed in Table 3 and graphically presented in FIGS. 7A-7C. Selected noncompartmental pharmacokinetic parameters following intravenous and oral dose are listed in Table 4.

TABLE 3

Plasma Concentration of Linezolid in Male Rats Following Intravenous and Oral Administration in Combo with Compound 101

| Time (hr) | Plasma Concentration (ng/mL) | | | | |
|---|---|---|---|---|---|
| IV-5 mg/kg | R1 | R2 | R3 | Mean | SD |
| 0 | BLQ | BLQ | BLQ | NA | NA |
| 0.083 | 6538.43 | 6357.70 | 6413.92 | 6436.68 | 92.49 |
| 0.25 | 6008.75 | 5524.99 | 4602.78 | 5378.84 | 714.29 |
| 0.5 | 5175.51 | 4239.64 | 4504.76 | 4639.97 | 482.36 |
| 1 | 3064.40 | 3520.08 | 3715.40 | 3433.29 | 334.06 |
| 2 | 1650.66 | 1866.66 | 1973.86 | 1830.39 | 164.62 |
| 4 | 351.22 | 559.76 | 603.17 | 504.72 | 134.69 |
| 6 | 41.91 | 152.65 | 134.87 | 109.81 | 59.47 |
| 8 | 14.30 | 47.59 | 24.88 | 28.92 | 17.01 |
| 10 | BLQ | 7.99 | 9.65 | 5.88 | 5.16 |
| 12 | BLQ | BLQ | BLQ | NA | NA |
| 24 | BLQ | BLQ | BLQ | NA | NA |
| PO-5 mg/kg | R4 | R5 | R6 | Mean | SD |
| 0 | BLQ | BLQ | BLQ | NA | NA |
| 0.083 | 2012.69 | 590.00 | 410.95 | 1004.55 | 877.65 |
| 0.25 | 3024.30 | 1278.49 | 1098.50 | 1800.43 | 1063.72 |
| 0.5 | 2864.08 | 1249.64 | 1329.78 | 1814.50 | 909.85 |
| 1 | 2330.63 | 1128.93 | 977.59 | 1479.05 | 741.36 |
| 2 | 1906.61 | 1014.40 | 1351.10 | 1424.04 | 450.55 |
| 4 | 990.16 | 435.42 | 510.20 | 645.26 | 301.03 |
| 6 | 321.68 | 72.99 | 100.41 | 165.03 | 136.36 |
| 8 | 90.93 | 12.16 | 19.42 | 40.84 | 43.53 |
| 10 | 19.42 | 0.00 | 0.00 | 6.47 | 11.21 |
| 12 | BLQ | BLQ | BLQ | NA | NA |
| 24 | BLQ | BLQ | BLQ | NA | NA |

TABLE 4

Selected Pharmacokinetics Parameters of linezolid in Rats Following Intravenous and Oral Administration in Combo with compound 101

| | AUC$_{(0-t)}$ µg/L * hr | AUC$_{(0-\infty)}$ µg/L * hr | MRT$_{(0-\infty)}$ hr | $t_{1/2z}$ hr | $T_{max}$ hr | $V_z$ L/kg | $CL_z$ L/hr/kg | $C_{max}$ µg/L | F % |
|---|---|---|---|---|---|---|---|---|---|
| IV-5 mg/kg | | | | | | | | | |
| R1 | 9868.77 | 9886.61 | 1.23 | 0.86 | 0.083 | 0.63 | 0.51 | 6538.43 | |
| R2 | 10787.50 | 10799.87 | 1.54 | 1.07 | 0.083 | 0.72 | 0.46 | 6357.70 | |
| R3 | 11047.43 | 11061.99 | 1.53 | 1.05 | 0.083 | 0.68 | 0.45 | 6413.92 | |
| mean | 10567.90 | 10582.82 | 1.44 | 0.99 | 0.083 | 0.68 | 0.47 | 6436.68 | |
| SD | 619.26 | 617.02 | 0.18 | 0.11 | 0 | 0.04 | 0.03 | 92.49 | |
| PO-5 mg/kg | | | | | | | | | |
| R4 | 9412.07 | 9416.52 | 2.33 | 0.86 | 0.25 | NA | NA | 3024.30 | 88.94 |
| R5 | 4223.37 | 4223.97 | 2.09 | 0.82 | 0.25 | NA | NA | 1278.49 | 39.91 |
| R6 | 4803.84 | 4803.91 | 2.24 | 0.52 | 2.00 | NA | NA | 1351.10 | 45.39 |
| mean | 6146.42 | 6148.13 | 2.22 | 0.73 | 0.83 | NA | NA | 1884.63 | 58.08 |
| SD | 2842.98 | 2845.32 | 0.12 | 0.18 | 1.01 | NA | NA | 987.65 | 26.86 |

NA: Not applicable

Following an IV combo administration of linezolid and compound 101 at a nominal dose of 5 mg/kg for each, the mean±SD value of systemic clearance for linezolid was 0.47±0.03 L/hr/kg, which corresponded to 14.20% of rat hepatic blood flow (3.31 L/hr/kg). The mean±SD value of half-life ($T_{1/2}$) for linezolid was 0.99±0.11 hr.

Following an IV combo administration of linezolid and compound 101 at a nominal dose of 5 mg/kg for each, the mean±SD values of $C_{max}$ (at 5 minutes after dosing) and $AUC_{(0-\infty)}$ for linezolid was 6436.68±92.49 µg/L and 10582.82±617.02 hr*µg/L. The volume of distribution at terminal phase was 0.68±0.04 L/kg, which corresponded to 101.49% of the total body water (0.67 L/kg) in the rats.

Following an oral combo administration of linezolid and compound 101 at a nominal dose of 5 mg/kg for each, the mean±SD values of $C_{max}$ and $T_{max}$ for linezolid were 1884.63±987.65 µg/L and 0.83±1.01 hr, respectively; the mean±SD values of $AUC_{(0-\infty)}$ and half-life ($T_{1/2}$) were 6148.13±2845.32 hr*µg/L and 0.73±0.18 hr, respectively. The mean±SD value of bioavailability for C-20079 was 58.08±26.86%.

Figure 8A:
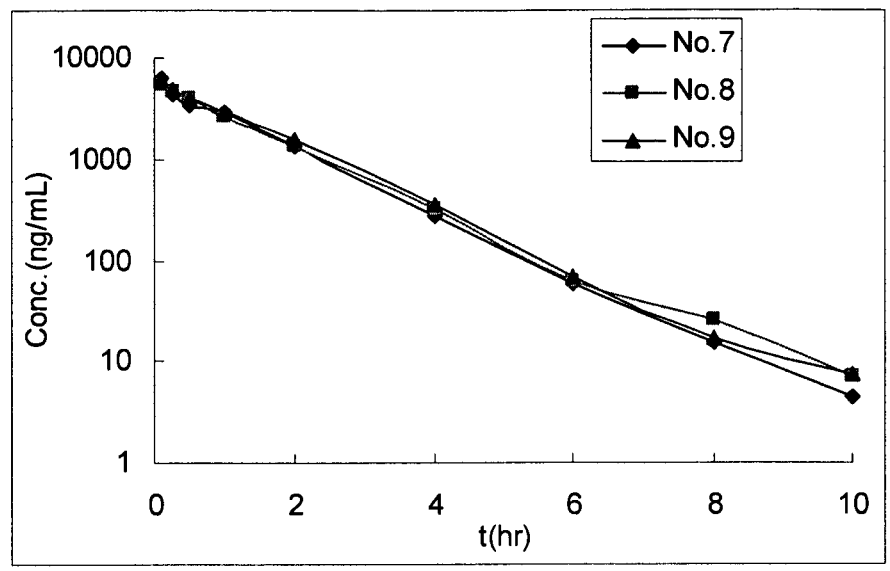
FIGS. 8A-8C depict concentration-time curve of linezolid in male rats following intravenous and oral administration linezolid in combination with compound 103.
Figure 8B:
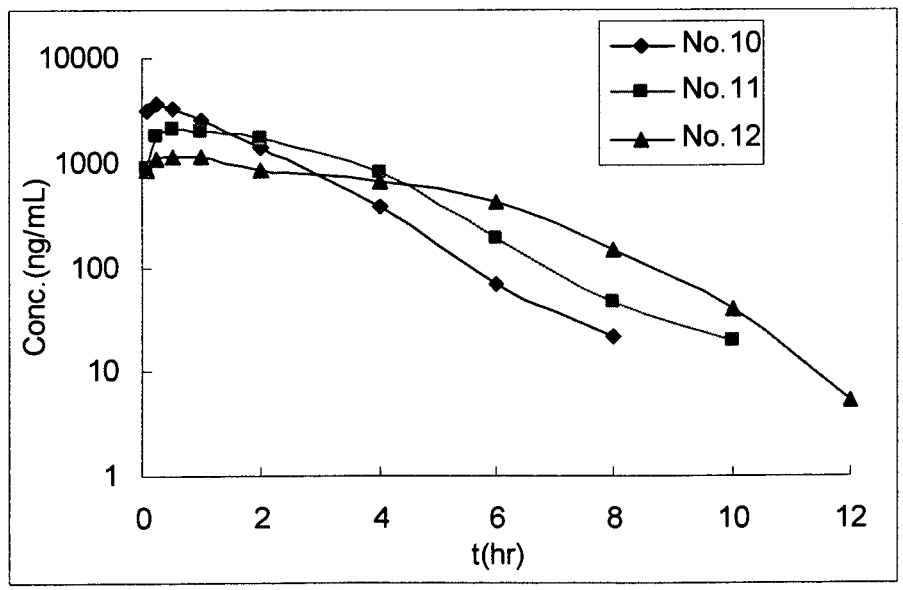
Figure 8C:
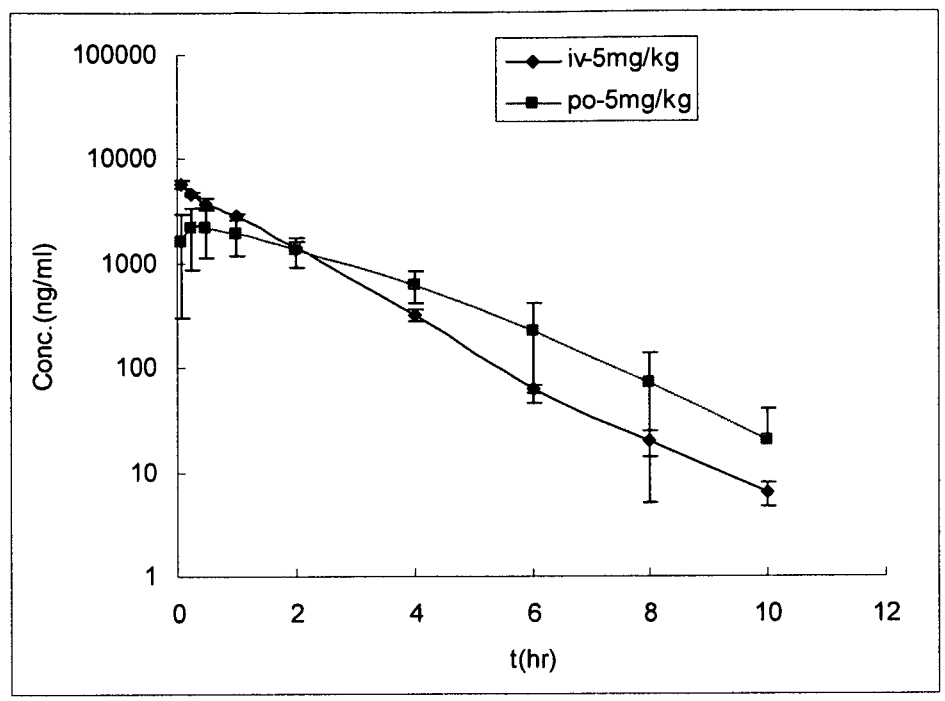

The individual and average concentration-time data of linezolid following intravenous and oral administration in combo with compound 103 are listed in Table 5 and graphically presented in FIGS. 8A-8C. Selected noncompartmental pharmacokinetic parameters following intravenous and oral dose are listed in Table 6.

TABLE 5

Plasma Concentration of Linezolid in Male Rats Following Intravenous and Oral Administration in Combo with Compound 103

| Time (hr) | Plasma Concentration (ng/mL) | | | | |
|---|---|---|---|---|---|
| IV-5 mg/kg | R7 | R8 | R9 | Mean | SD |
| 0 | BLQ | BLQ | BLQ | NA | NA |
| 0.083 | 6324.03 | 5309.66 | 5983.54 | 5872.41 | 516.24 |
| 0.25 | 4352.05 | 4727.02 | 4742.46 | 4607.18 | 221.08 |
| 0.5 | 3323.69 | 3959.46 | 4045.58 | 3776.24 | 394.28 |
| 1 | 2919.08 | 2636.07 | 2835.48 | 2796.88 | 145.40 |
| 2 | 1361.81 | 1350.43 | 1596.24 | 1436.16 | 138.75 |
| 4 | 278.33 | 320.60 | 361.30 | 320.08 | 41.49 |
| 6 | 58.01 | 61.51 | 69.63 | 63.05 | 5.96 |
| 8 | 15.53 | 26.06 | 16.75 | 19.45 | 5.76 |
| 10 | 4.46 | 7.24 | 7.29 | 6.33 | 1.62 |
| 12 | 0 | 0 | 0 | NA | NA |
| 24 | 0 | 0 | 0 | NA | NA |
| PO-5 mg/kg | R10 | R11 | R12 | Mean | SD |
| 0 | 0 | 0 | 0 | NA | NA |
| 0.083 | 3117.08 | 872.70 | 829.97 | 1606.58 | 1308.30 |
| 0.25 | 3594.56 | 1764.67 | 1099.44 | 2152.89 | 1292.07 |
| 0.5 | 3266.77 | 2142.20 | 1132.83 | 2180.60 | 1067.49 |
| 1 | 2544.56 | 1964.34 | 1169.57 | 1892.82 | 690.28 |
| 2 | 1424.06 | 1728.58 | 860.03 | 1337.56 | 440.69 |
| 4 | 382.80 | 789.74 | 664.96 | 612.50 | 208.48 |
| 6 | 70.20 | 184.51 | 420.25 | 224.99 | 178.50 |
| 8 | 21.39 | 46.16 | 146.45 | 71.33 | 66.22 |
| 10 | 0.00 | 19.47 | 40.28 | 19.92 | 20.14 |
| 12 | 0.00 | 0.00 | 5.15 | 1.72 | 2.97 |
| 24 | 0.00 | 0.00 | 0.00 | NA | NA |

SD: Standard deviation;
NA: Not applicable, or failed to collect samples.

TABLE 6

Selected Pharmacokinetics Parameters of linezolid in Rats Following Intravenous and Oral Administration in Combo with compound 103

| | $AUC_{(0-t)}$ µg/L * hr | $AUC_{(0-\infty)}$ µg/L * hr | $MRT_{(0-\infty)}$ hr | $t_{1/2z}$ hr | $T_{max}$ hr | $V_z$ L/kg | $CL_z$ L/hr/kg | $C_{max}$ µg/L | F % |
|---|---|---|---|---|---|---|---|---|---|
| IV-5 mg/kg | | | | | | | | | |
| R1 | 8200.53 | 8207.49 | 1.28 | 1.08 | 0.083 | 0.95 | 0.61 | 6324.03 | |
| R2 | 8193.82 | 8204.53 | 1.34 | 1.03 | 0.083 | 0.90 | 0.61 | 5309.66 | |
| R3 | 8956.18 | 8966.61 | 1.36 | 0.99 | 0.083 | 0.80 | 0.56 | 5983.54 | |
| mean | 8450.17 | 8459.54 | 1.33 | 1.03 | 0.083 | 0.88 | 0.59 | 5646.60 | |
| SD | 438.23 | 439.14 | 0.04 | 0.05 | 0 | 0.08 | 0.03 | 476.51 | |
| PO-5 mg/kg | | | | | | | | | |
| R4 | 7361.11 | 7366.21 | 1.54 | 0.96 | 0.25 | NA | NA | 3594.56 | 87.02 |
| R5 | 7429.44 | 7434.26 | 2.28 | 1.04 | 0.5 | NA | NA | 2142.20 | 87.82 |
| R6 | 5474.04 | 5480.19 | 3.17 | 0.83 | 1 | NA | NA | 1169.57 | 64.71 |
| mean | 6754.86 | 6760.22 | 2.33 | 0.94 | 0.58 | NA | NA | 2302.11 | 79.85 |
| SD | 1109.75 | 1109.06 | 0.82 | 0.11 | 0.38 | NA | NA | 1220.38 | 13.12 |

Following an IV combo administration of linezolid and compound 103 at a nominal dose of 5 mg/kg for each, the mean±SD value of systemic clearance for linezolid was 0.59±0.03 L/hr/kg, which corresponded to 17.82% of rat hepatic blood flow (3.31 L/hr/kg). The mean±SD value of half-life ($T_{1/2}$) for linezolid was 1.03±0.05 hr.

Following an IV combo administration of linezolid and compound 103 at a nominal dose of 5 mg/kg for each, the mean±SD values of $C_{max}$ (at 5 minutes after dosing) and $AUC_{(0-\infty)}$ for linezolid was 5646.60±476.51 μg/L and 8459.54±439.14 hr*μg/L. The volume of distribution at terminal phase was 0.88±0.08 L/kg, which corresponded to 131.34% of the total body water (0.67 L/kg) in the rats.

Following an oral combo administration of linezolid and compound 103 at a nominal dose of 5 mg/kg for each, the mean±SD values of $C_{max}$ and $T_{max}$ for inezolid were 2302.11±1220.38 μg/L and 0.58±0.38 hr, respectively; the mean±SD values of $AUC_{(0-\infty)}$ and half-life ($T_{1/2}$) were 6760.22±1109.06 hr*μg/L and 0.94±0.11 hr, respectively. The mean±SD value of bioavailability for inezolid was 79.85±13.12%.

Pharmacokinetics of Compound 101 after Combinatory Administration

Figure 9A:
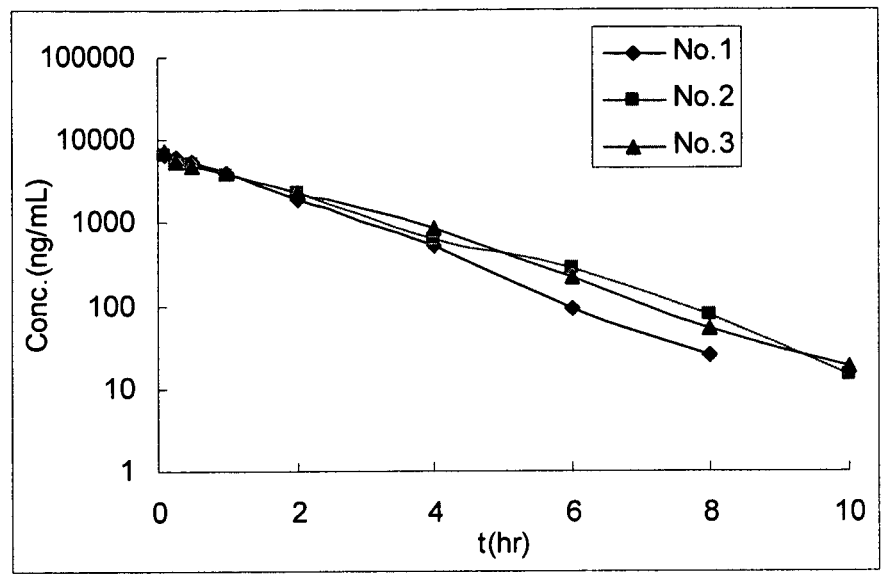
FIGS. 9A-9C depict concentration-time curve of compound 101 in male rats following intravenous and oral administration of compound 101 in combination with compound linezolid.
Figure 9B:
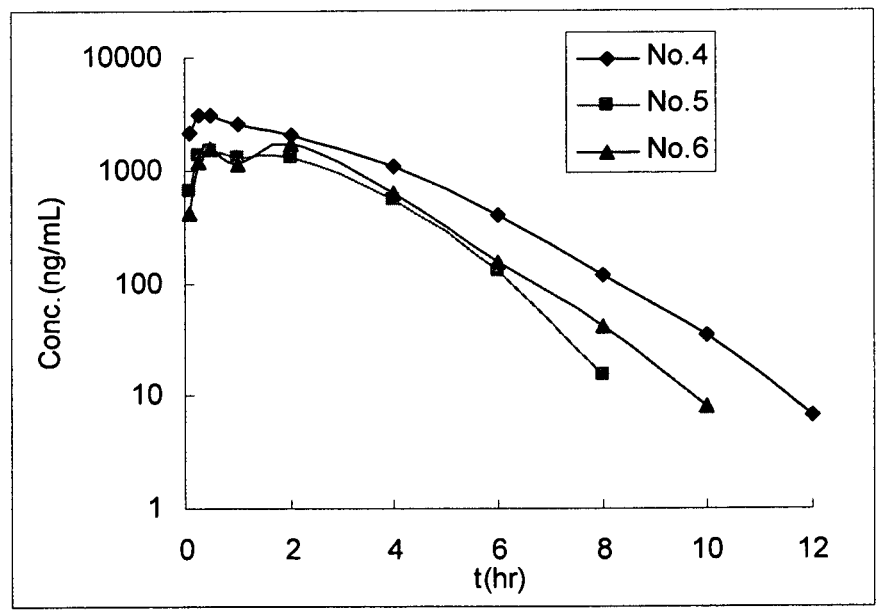
Figure 9C:
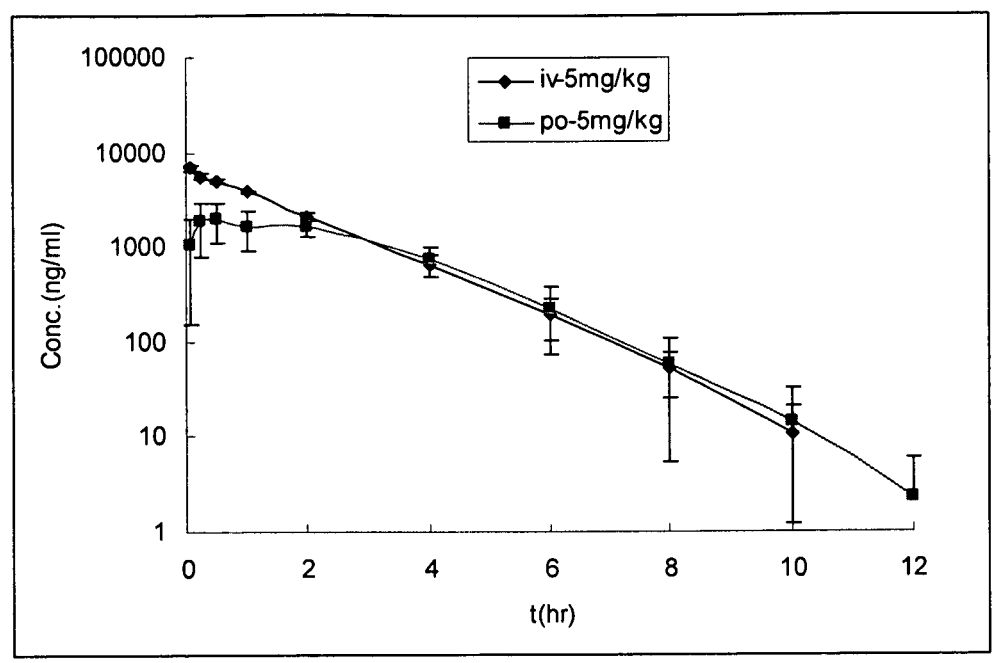

The individual and average concentration-time data of compound 101 following intravenous and oral administration in combo with linezolid are listed in Table 7 and graphically presented in FIGS. 9A-9C. Selected noncompartmental pharmacokinetic parameters following intravenous and oral dose are listed in Table 8.

TABLE 7

Plasma Concentration of Compound 101 in Male Rats Following Intravenous and Oral Administration in Combo with Linezolid

| Time (hr) | Plasma Concentration (ng/mL) | | | | |
|---|---|---|---|---|---|
| IV-5 mg/kg | R1 | R2 | R3 | Mean | SD |
| 0 | BLQ | BLQ | BLQ | NA | NA |
| 0.083 | 6719.44 | 6416.06 | 7425.71 | 6853.74 | 518.05 |
| 0.25 | 6101.94 | 5331.52 | 5420.88 | 5618.11 | 421.38 |
| 0.5 | 5364.69 | 5044.74 | 4848.40 | 5085.94 | 260.60 |
| 1 | 3963.43 | 3753.70 | 3932.93 | 3883.35 | 113.31 |
| 2 | 1878.69 | 2256.33 | 2224.16 | 2119.73 | 209.36 |
| 4 | 509.38 | 639.49 | 827.10 | 658.65 | 159.73 |
| 6 | 93.28 | 275.64 | 213.94 | 194.29 | 92.75 |
| 8 | 25.40 | 77.51 | 52.37 | 51.76 | 26.06 |
| 10 | 0.00 | 14.23 | 18.65 | 10.96 | 9.74 |
| 12 | BLQ | BLQ | BLQ | NA | NA |
| 24 | BLQ | BLQ | BLQ | NA | NA |
| PO-5 mg/kg | R4 | R5 | R6 | Mean | SD |
| 0 | BLQ | BLQ | BLQ | NA | NA |
| 0.083 | 2104.47 | 665.55 | 424.98 | 1065.00 | 908.21 |
| 0.25 | 3126.75 | 1347.04 | 1169.00 | 1880.93 | 1082.58 |
| 0.5 | 3079.25 | 1458.73 | 1549.49 | 2029.16 | 910.54 |
| 1 | 2539.95 | 1313.41 | 1131.52 | 1661.63 | 766.07 |
| 2 | 2009.31 | 1275.29 | 1680.83 | 1655.14 | 367.68 |
| 4 | 1064.86 | 556.90 | 638.81 | 753.52 | 272.72 |
| 6 | 406.47 | 127.45 | 153.40 | 229.11 | 154.15 |
| 8 | 115.90 | 15.32 | 41.63 | 57.62 | 52.16 |
| 10 | 34.73 | 0.00 | 8.11 | 14.28 | 18.17 |
| 12 | 6.72 | 0.00 | 0.00 | 2.24 | 3.88 |
| 24 | BLQ | BLQ | BLQ | NA | NA |

TABLE 8

Selected Pharmacokinetics Parameters of Compound 101 in Rats Following Intravenous and Oral Administration in Combo with Linezolid

| | $AUC_{(0-t)}$ μg/L * hr | $AUC_{(0-\infty)}$ μg/L * hr | $MRT_{(0-\infty)}$ hr | $t_{1/2z}$ hr | $T_{max}$ hr | $V_z$ L/kg | $CL_z$ L/hr/kg | $C_{max}$ μg/L | F % |
|---|---|---|---|---|---|---|---|---|---|
| IV-5 mg/kg | | | | | | | | | |
| R1 | 11467.98 | 11474.53 | 1.37 | 0.95 | 0.083 | 0.60 | 0.44 | 6719.44 | |
| R2 | 12296.61 | 12320.88 | 1.71 | 1.18 | 0.083 | 0.69 | 0.41 | 6416.06 | |
| R3 | 12728.36 | 12759.67 | 1.68 | 1.16 | 0.083 | 0.66 | 0.39 | 7425.71 | |
| mean | 12164.32 | 12185.03 | 1.59 | 1.10 | 0.083 | 0.65 | 0.41 | 6853.74 | |
| SD | 640.52 | 653.25 | 0.19 | 0.13 | 0 | 0.05 | 0.02 | 518.05 | |
| PO-5 mg/kg | | | | | | | | | |
| R4 | 10239.29 | 10249.23 | 2.43 | 1.03 | 0.25 | NA | NA | 3126.75 | 84.03 |
| R5 | 5193.09 | 5210.14 | 2.19 | 0.77 | 0.50 | NA | NA | 1458.73 | 42.62 |
| R6 | 5923.60 | 5934.87 | 2.37 | 0.96 | 2.00 | NA | NA | 1680.83 | 48.61 |
| mean | 7118.66 | 7832.03 | 2.33 | 0.92 | 0.92 | NA | NA | 2088.77 | 58.42 |
| SD | 2727.12 | 4713.42 | 0.12 | 0.13 | 0.95 | NA | NA | 905.75 | 22.38 |

Following an IV combo administration of compound 101 and linezolid at a nominal dose of 5 mg/kg for each, the mean±SD value of systemic clearance for compound 101 was 0.41±0.02 L/hr/kg, which corresponded to 12.39% of rat hepatic blood flow (3.31 L/hr/kg). The mean±SD value of half-life ($T_{1/2}$) for compound 101 was 1.10±0.13 hr.

Following an IV combo administration of compound 101 and linezolid at a nominal dose of 5 mg/kg for each, the mean±SD values of $C_{max}$ (at 5 minutes after dosing) and $AUC_{(0-\infty)}$ for compound 101 was 6853.74±518.05 μg/L and 12185.03±653.25 hr*μg/L. The volume of distribution at terminal phase was 0.65±0.05 L/kg, which corresponded to 97.01% of the total body water (0.67 L/kg) in the rats.

Following an oral combo administration of compound 101 and linezolid at a nominal dose of 5 mg/kg for each, the mean±SD values of $C_{max}$ and $T_{max}$ for compound 101 were 2088.77±905.75 μg/L and 0.92±0.95 hr, respectively; the mean±SD values of $AUC_{(0-\infty)}$ and half-life ($T_{1/2}$) were 7832.03±4713.42 hr*μg/L and 0.92±0.13 hr, respectively. The mean±SD value of bioavailability for compound 101 was 58.42±22.38%.

Pharmacokinetics of Compound 103 after Combinatory Administration

Figure 10A:
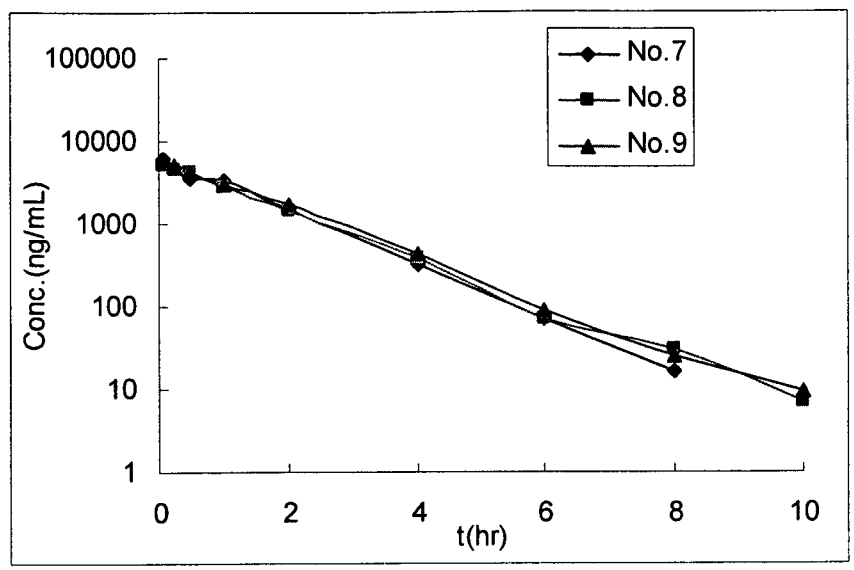
FIGS. 10A-10C depict concentration-time curve of compound 103 in male rats following intravenous and oral administration of compound 103 in combination with compound linezolid.
Figure 10B:
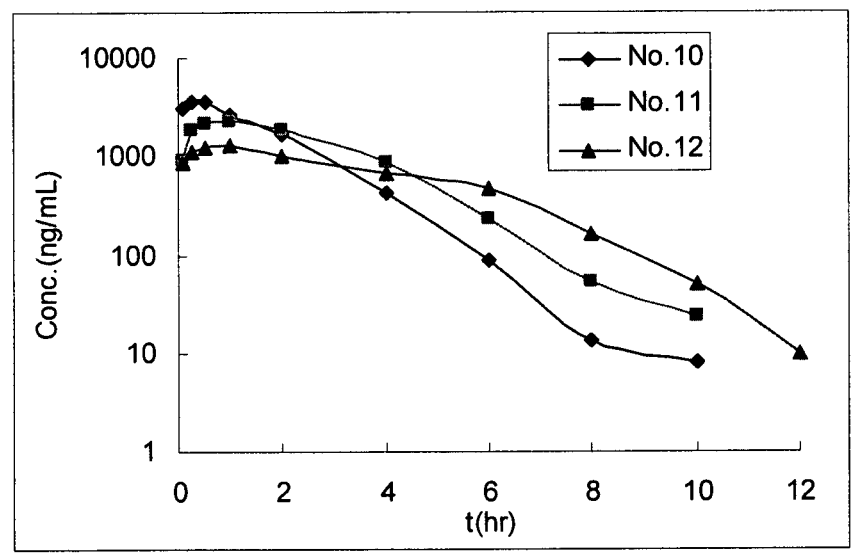
Figure 10C:
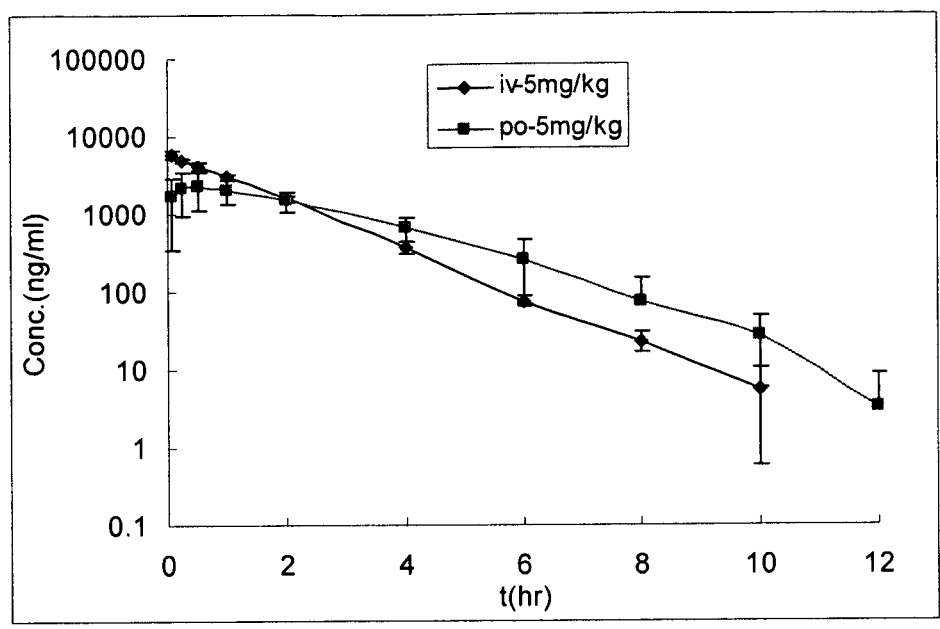

The individual and average concentration-time data of compound 103 following intravenous and oral administration in combo with linezolid are listed in Table 9 and graphically presented in FIGS. 10A-10C Selected noncompartmental pharmacokinetic parameters following intravenous and oral dose are listed in Table 10.

TABLE 9

Plasma Concentration of Compound 103 in Male Rats Following Intravenous and Oral Administration in Combo with Linezolid

| Time (hr) | Plasma Concentration (ng/mL) | | | | |
|---|---|---|---|---|---|
| IV-5 mg/kg | R7 | R8 | R9 | Mean | SD |
| 0 | BLQ | BLQ | BLQ | NA | NA |
| 0.083 | 6239.85 | 5226.29 | 6160.63 | 5875.59 | 563.70 |
| 0.25 | 4729.24 | 4608.04 | 5155.86 | 4831.05 | 287.75 |
| 0.5 | 3590.16 | 4254.51 | 4412.69 | 4085.79 | 436.45 |
| 1 | 3305.80 | 2745.30 | 2985.25 | 3012.12 | 281.21 |
| 2 | 1517.70 | 1452.58 | 1736.63 | 1568.97 | 148.80 |
| 4 | 319.18 | 368.42 | 438.89 | 375.50 | 60.17 |
| 6 | 70.89 | 70.76 | 88.03 | 76.56 | 9.93 |
| 8 | 15.94 | 29.51 | 25.09 | 23.51 | 6.92 |
| 10 | 0.00 | 7.06 | 9.53 | 5.53 | 4.95 |
| 12 | BLQ | BLQ | BLQ | NA | NA |
| 24 | BLQ | BLQ | BLQ | NA | NA |
| PO-5 mg/kg | R10 | R11 | R12 | Mean | SD |
| 0 | BLQ | BLQ | BLQ | NA | NA |
| 0.083 | 3177.06 | 913.00 | 887.24 | 1659.10 | 1314.65 |
| 0.25 | 3577.65 | 1842.44 | 1122.93 | 2181.01 | 1261.90 |
| 0.5 | 3586.70 | 2137.40 | 1218.21 | 2314.10 | 1194.09 |
| 1 | 2683.05 | 2253.76 | 1281.26 | 2072.69 | 718.22 |
| 2 | 1649.99 | 1843.14 | 1017.10 | 1503.41 | 432.09 |
| 4 | 430.42 | 861.28 | 682.57 | 658.09 | 216.47 |
| 6 | 89.36 | 229.10 | 467.14 | 261.87 | 191.01 |
| 8 | 13.39 | 52.04 | 160.20 | 75.21 | 76.10 |
| 10 | 7.90 | 23.83 | 50.81 | 27.51 | 21.69 |
| 12 | 0.00 | 0.00 | 9.71 | 3.24 | 5.61 |
| 24 | BLQ | BLQ | BLQ | NA | NA |

TABLE 10

Selected Pharmacokinetics Parameters of Compound 103 in Rats Following Intravenous and Oral Administration in Combo with Linezolid

| | $AUC_{(0-t)}$ μg/L * hr | $AUC_{(0-\infty)}$ μg/L * hr | $MRT_{(0-\infty)}$ hr | $t_{1/2z}$ hr | $T_{max}$ hr | $V_z$ L/kg | $CL_z$ L/hr/kg | $C_{max}$ μg/L | F % |
|---|---|---|---|---|---|---|---|---|---|
| IV-5 mg/kg | | | | | | | | | |
| R1 | 8978.23 | 8979.14 | 1.30 | 0.83 | 0.083 | 0.67 | 0.56 | 6239.85 | |
| R2 | 8631.63 | 8634.33 | 1.39 | 1.00 | 0.083 | 0.84 | 0.58 | 5226.29 | |
| R3 | 9736.59 | 9750.85 | 1.42 | 1.04 | 0.083 | 0.77 | 0.51 | 6160.63 | |
| mean | 9115.48 | 9121.44 | 1.37 | 0.96 | 0.083 | 0.76 | 0.55 | 5693.46 | |
| SD | 565.13 | 571.70 | 0.06 | 0.11 | 0 | 0.09 | 0.04 | 660.68 | |
| PO-5 mg/kg | | | | | | | | | |
| R4 | 8049.61 | 8061.08 | 1.59 | 1.01 | 0.50 | NA | NA | 3586.70 | 88.25 |
| R5 | 8090.94 | 8096.42 | 2.32 | 1.05 | 1.00 | NA | NA | 2253.76 | 88.70 |
| R6 | 6019.61 | 6034.82 | 3.19 | 1.09 | 1.00 | NA | NA | 1281.26 | 65.99 |
| mean | 7386.72 | 6939.38 | 2.37 | 1.05 | 0.83 | NA | NA | 2373.91 | 80.98 |
| SD | 1184.13 | 3365.36 | 0.80 | 0.04 | 0.29 | NA | NA | 1157.41 | 12.98 |

Following an IV combo administration of compound 103 and linezolid at a nominal dose of 5 mg/kg for each, the mean±SD value of systemic clearance for compound 103 was 0.55±0.04 L/hr/kg, which corresponded to 16.62% of rat hepatic blood flow (3.31 L/hr/kg). The mean±SD value of half-life ($T_{1/2}$) for compound 103 was 0.96±0.11 hr.

Following an IV combo administration of compound 103 and linezolid at a nominal dose of 5 mg/kg for each, the mean±SD values of $C_{max}$ (at 5 minutes after dosing) and $AUC_{(0-\infty)}$ for compound 103 was 5693.46±660.68 µg/L and 9121.44±571.70 hr*µg/L. The volume of distribution at terminal phase was 0.76±0.09 L/kg, which corresponded to 113.43% of the total body water (0.67 L/kg) in the rats.

Following an oral combo administration of compound 103 and linezolid at a nominal dose of 5 mg/kg for each, the mean±SD values of $C_{max}$ and $T_{max}$ for compound 103 were 2373.91±1157.41 µg/L and 0.83±0.29 hr, respectively; the mean±SD values of $AUC_{(0-\infty)}$ and half-life ($T_{1/2}$) were 6939.38±3365.36 hr*µg/L and 1.05±0.04 hr, respectively. The mean±SD value of bioavailability for compound 103 was 80.98±12.98%.

Conclusions

Following combo IV injection with compound 101, the mean values of systemic clearance and half-life for linezolid were 0.47 L/hr/kg and 0.99 hr, respectively; the mean value of $V_z$ was 0.68 L/kg. The mean value of bioavailability after oral administration for linezolid was 58.08%.

Following combo IV injection with compound 103, the mean values of systemic clearance and half-life for linezolid were 0.59 L/hr/kg and 1.03 hr, respectively; the mean value of $V_z$ was 0.88 L/kg. The mean value of bioavailability after oral administration for linezolid was 79.85%.

Following combo IV injection with linezolid, the mean values of systemic clearance and half-life for compound 101 were 0.41 L/hr/kg and 1.10 hr, respectively; the mean value of $V_z$ was 0.65 L/kg. The mean value of bioavailability after oral administration for compound 101 was 58.42%.

Following combo IV injection with linezolid, the mean values of systemic clearance and half-life for compound 103 were 0.55 L/hr/kg and 0.96 hr, respectively; the mean value of $V_z$ was 0.76 L/kg. The mean value of bioavailability after oral administration for compound 103 was 80.98%.

Figure 11:
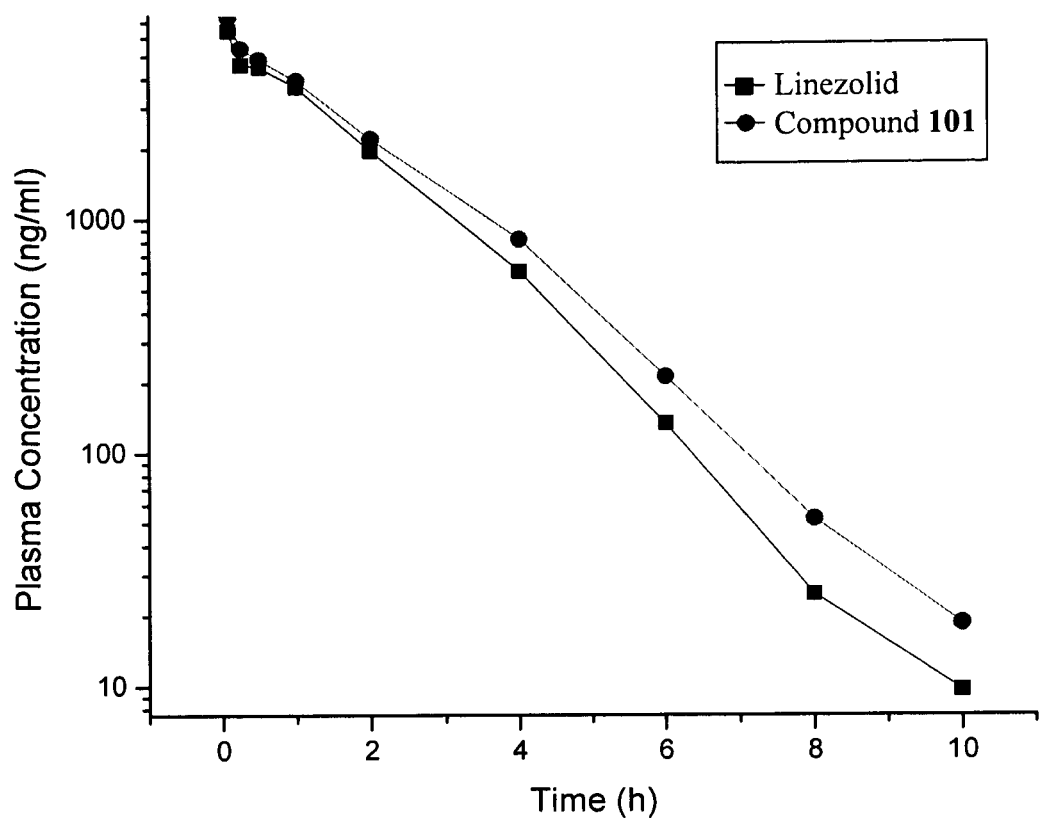
FIG. 11 is a plot showing mean plasma concentration of linezolid (-■-) and compound 101 (-●-) versus time following intravenous administration of linezolid and compound 101.
Figure 12:
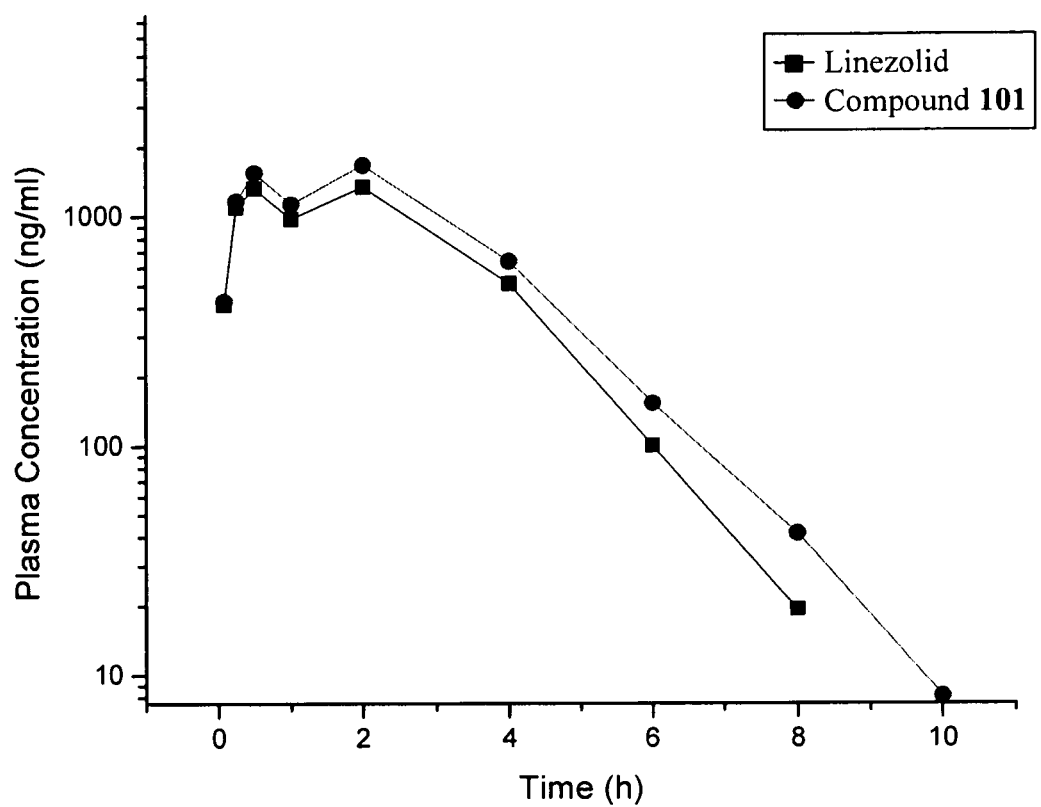
FIG. 12 is a plot showing mean plasma concentration of linezolid (-■-) and compound 101 (-●-) versus time following oral administration of linezolid and compound 101.
Figure 13:
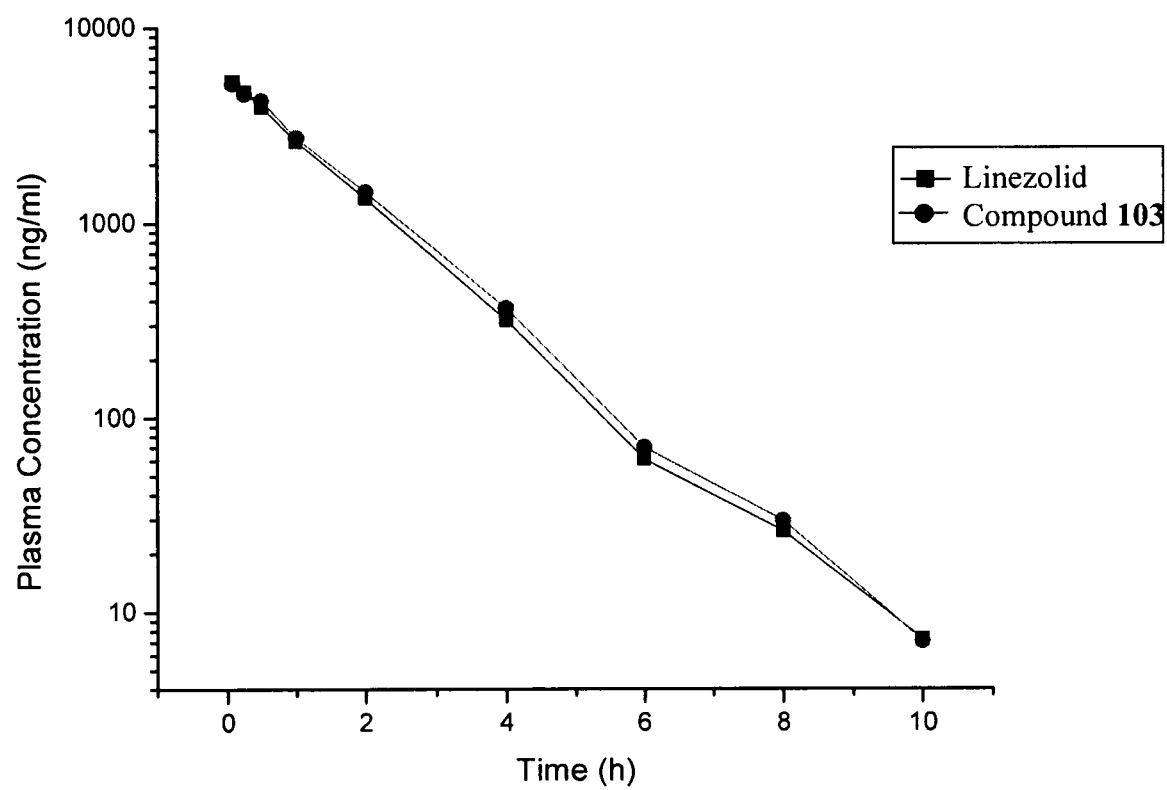
FIG. 13 is a plot showing mean plasma concentration of linezolid (-■-) and compound 103 (-●-) versus time following intravenous administration of linezolid and compound 103.
Figure 14:
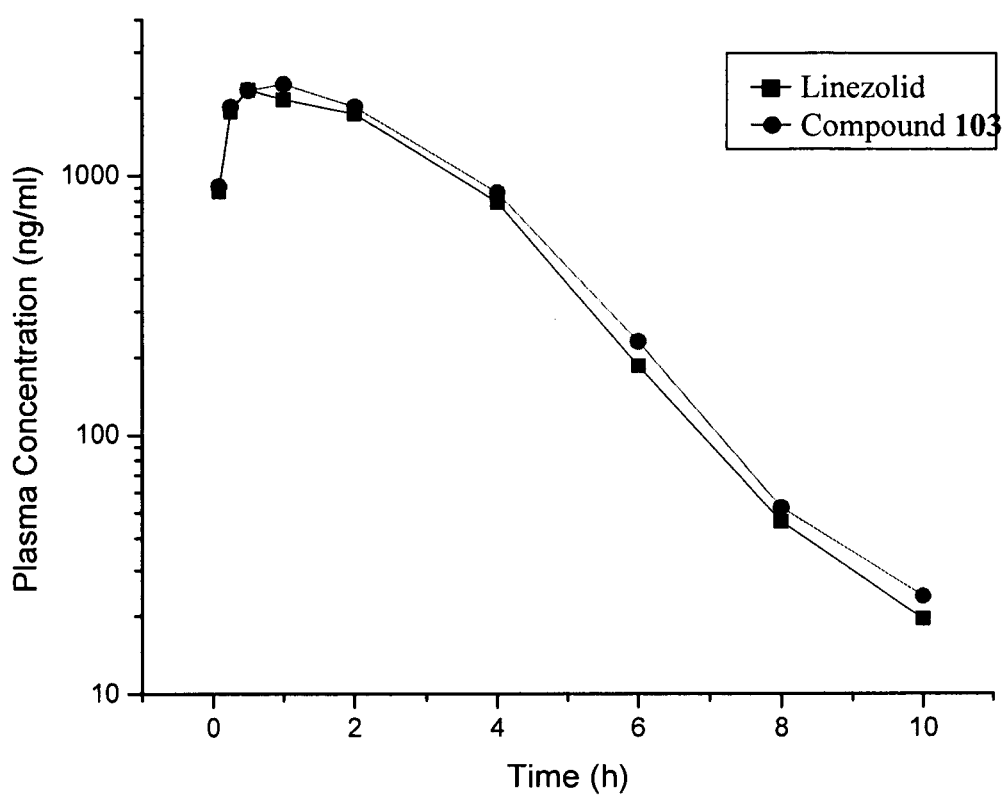
FIG. 14 is a plot showing mean plasma concentration of linezolid (-■-) and compound 103 (-●-) versus time following oral administration of linezolid and compound 103.

A graph showing the mean plasma concentration of linezolid and compound 101 over time following intravenous injection of a combination of linezolid and compound 101 is shown in FIG. 11. A graph showing the mean plasma concentration of linezolid and compound 101 over time following oral administration of a combination of linezolid and compound 101 is shown in FIG. 12. A graph showing the mean plasma concentration of linezolid and compound 103 over time following intravenous injection of a combination of linezolid and compound 103 is shown in FIG. 13. A graph showing the mean plasma concentration of linezolid and compound 103 over time following oral administration of a combination of linezolid and compound 103 is shown in FIG. 14.

Example 17

Pharmacokinetics in Chimpanzees

The pharmacokinetics of compounds 100 and 101 when administered to chimpanzees orally or intravenously in a 50:50 mixture with linezolid were studied. The solution for both oral and intravenous administration was prepared by combining linezolid (200 mg), compound 100 (200 mg), sodium citrate dihydrate (164 mg), anhydrous citric acid (85 mg), and dextrose monohydrate (5.024 g) in 900 ml of sterile water for injection at 65° C. with stirring. The mixture was cooled to 25° C. and the pH of the resulting solution adjusted to 4.8 with either 10% HCl or 10% NaOH as needed. The final volume of the solution was brought up to 1 l with sterile water. The dosing solution is then filtered through a 0.22 µm filter prior to dosing.

Four chimpanzees (two male and two female) were used in the study. One male and one female were used for the intravenous study and one male and one female were used for the oral dosing study. All animals were fasted overnight prior to dosing. For all studies animals were sedated with ketamine (approx. 10 mg/ml) or telazol (approx. 5 mg/ml) prior to dosing. For each study animals were dosed with 300 mg of the combined drugs (150 mg each of linezolid and compound 100). Intravenous doses were administered (150 ml at 2 mg/ml combined drugs) by infusion over a 30 minute period. Oral doses were administered in a volume of 150 ml at 2 mg/ml combined drugs.

For the intravenous study, a 4.5 ml aliquot of blood was taken from each animal prior to the start of infusion, 15 minutes after the start of infusion, and immediately before the end of infusion. Additional samples were taken at 6, 15, 30, and 60 minutes and 1.5, 2, 4, 6, 8 and 24 hours following infusion. For the oral study, 4.5 ml aliquots of blood were taken from each animal prior to doing and then at 15, 20 and 60 minutes and 1.5, 2, 4, 6, 8 and 24 hours post dosing. All blood samples were collected into vacutainer tubes containing sodium heparin as an anticoagulant, sufficiently mixed and stored on wet ice. The samples were centrifuged within 1 hour of collection and the plasma collected and frozen at −70° C. until analysis. Urine was also collected from each animal over a 24 hour period following dosing.

Each sample was analyzed by LC-MS/MS for the presence of both linezolid and compound 100 as follows. Chimp plasma sample (100 µL) was mixed with 300 µL internal standard solution prior to LC-MS/MS analysis. The internal standard was 250 ng/mL haloperidol in acetonitrile/water (90/10, v/v). After protein precipitation, 10 L supernatant was injected to a Zorbax SB-C8 (Rapid Resolution) column (2.1× 30 mm, 3.5 µm). The initial mobile phase condition was 100% A (water with 0.1% formic acid) and 0% B (acetonitrile with 0.1% formic acid) with a flow rate at 0.5 mL/min. Mobile phase B was allowed to reach 90% within 2 minutes and held for 1 minute before ramping back 0% at 3.2 minutes. The overall run time was six minutes. The precursor/product ion pairs were set at m/z 338/296, m/z 348/306 and m/z 376/165 for detecting linezolid, Compound 100 and haloperidol, respectively.

Urine samples were similarly analyzed. Chimp urine samples (10 µL) were independently injected to a Zorbax SB-C8 (Rapid Resolution) column (2.1×30 mm, 3.5 µm). The initial mobile phase condition was 100% A (water with 0.1% formic acid) and 0% B (acetonitrile with 0.1% formic acid) with a flow rate at 0.4 mL/min. Mobile phase B was allowed to reach 25% within 42 minutes and then from 25% to 90% in two minutes before ramping back 0% in four minutes. The overall run time was 48 minutes. The mass spectrometer was set in positive ion mode and ions were scanned from m/z 100 to 1000. Once certain molecular ions of metabolites were identified, MS/MS experiments were carried out to produce product ions.

The pharmacokinetics of compound 101 was studied according the protocol described above.

Figure 2:
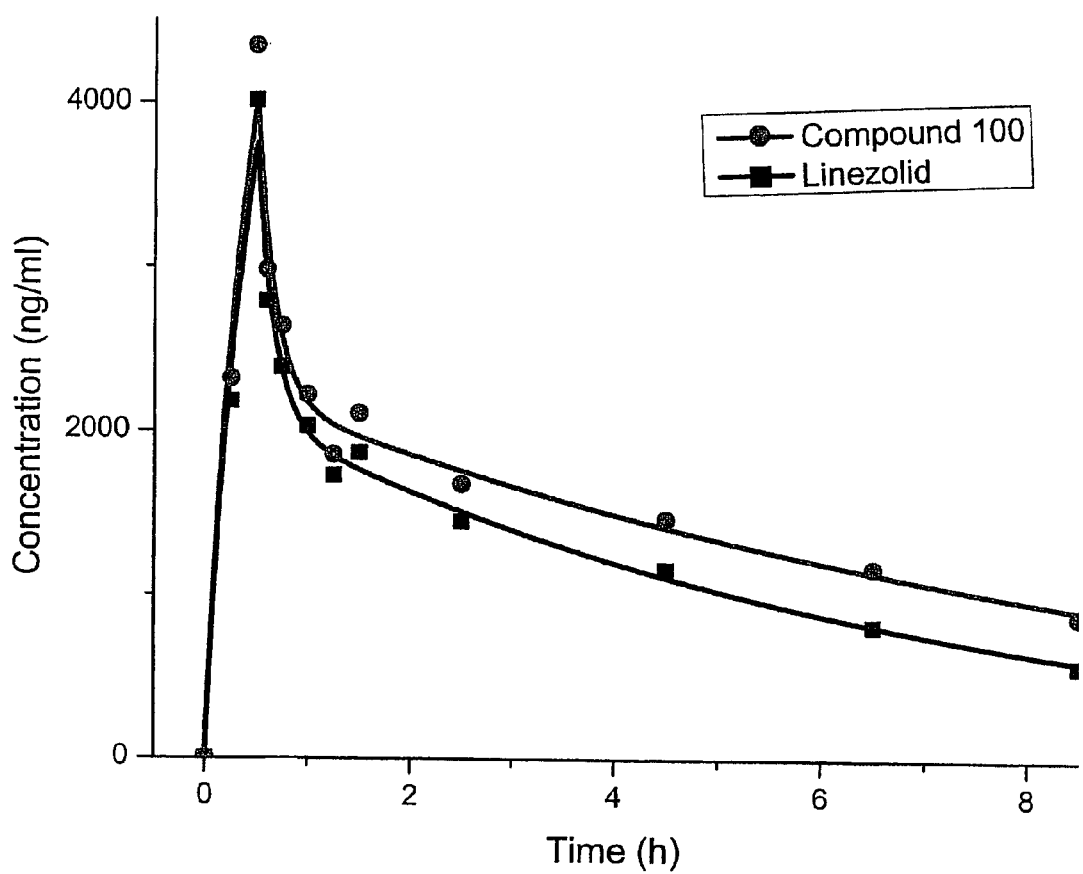
FIG. 2 depicts the serum pharmacokinetics of a combination of linezolid and Compound 100 following intravenous infusion into a male chimpanzee.

FIGS. 1 and 2 show the results of the intravenous dosing study for compound 100. Both the female (FIG. 1) and male chimpanzee (FIG. 2) exhibited an increased half-life and AUC for compound 100 as compared to linezolid. The calculated half-lives for IV dosing are shown in Table 11.

TABLE 11

Half-lives of compound 100 and linezolid following intravenous dosing

| Drug | Half-life (Female) | Half-life (Male) |
| --- | --- | --- |
| Linezolid | 4.5 h | 4.5 h |
| Compound 100 | 6.4 h | 6.2 h |

Figure 3:
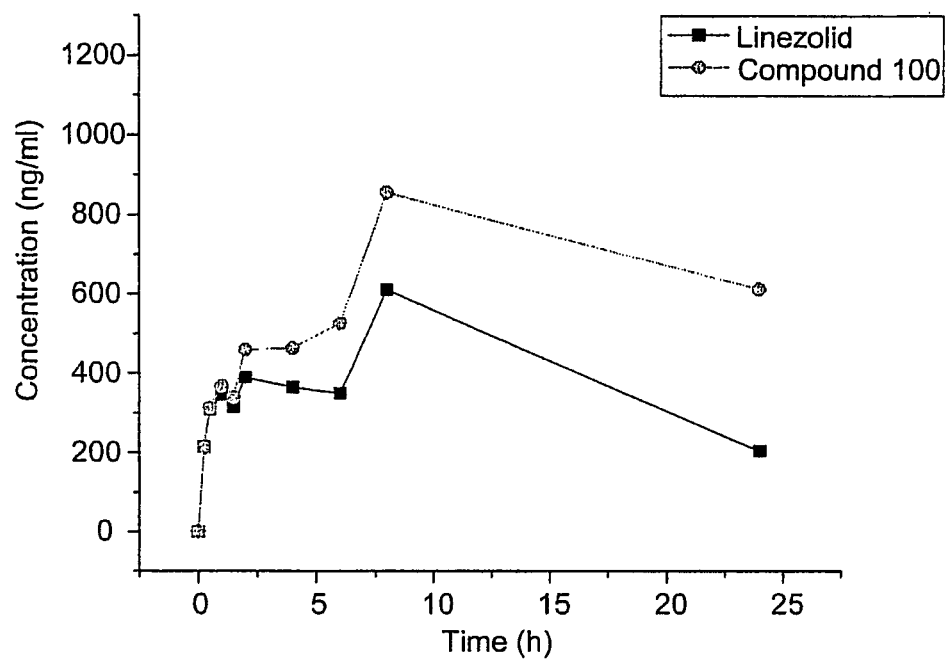
FIG. 3 depicts the serum pharmacokinetics of a combination of linezolid and Compound 100 following oral administration to a female chimpanzee.
Figure 4:
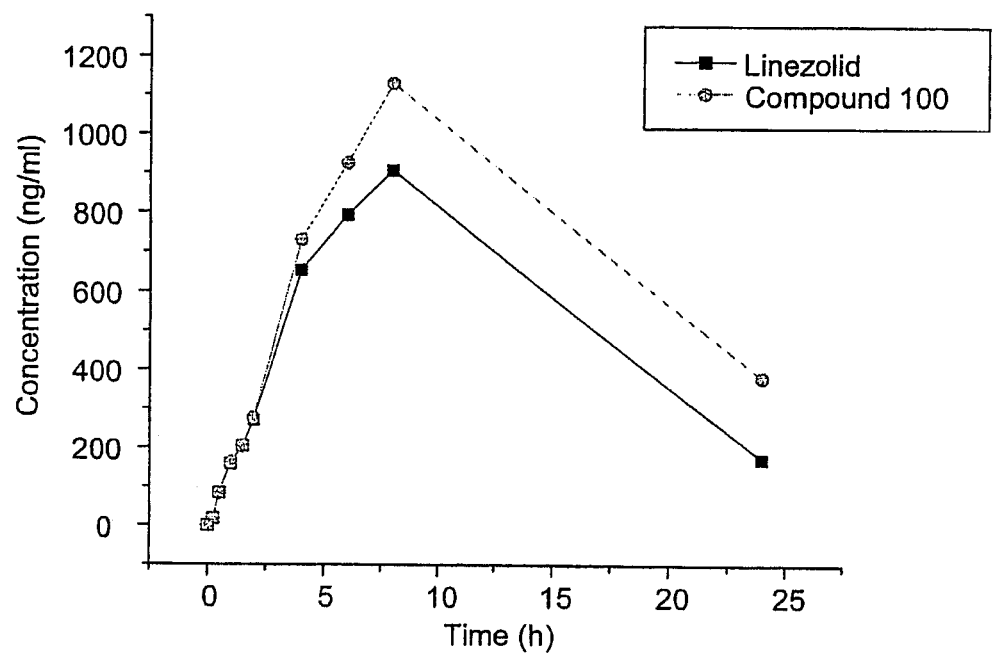
FIG. 4 depicts the serum pharmacokinetics of a combination of linezolid and Compound 100 following oral administration to a male chimpanzee.

FIGS. 3 and 4 show the results of the oral dosing study for compound 100. Both the female (FIG. 3) and male chimpanzee (FIG. 4) exhibited an increased half-life and AUC for compound 100 as compared to linezolid. The ratio of serum concentration of compound 100 to linezolid at 8 and 24 hours is shown in Table 12. The mean calculated AUC for each compound is set forth in Table 13.

TABLE 12

Ratio of serum concentration of compound 100 to linezolid following oral dosing.

| Time post-dosing | Ratio (compound 100:linezolid) Female | Ratio (compound 100:linezolid) Male |
| --- | --- | --- |
| 8 h | 1.39 | 1.20 |
| 24 h | 2.99 | 2.20 |

TABLE 13

Mean $AUC_{0\text{-}24\,h}$ of compound 100 and linezolid following oral dosing

| Compound | Mean $AUC_{0\text{-}24\,h}$ (ng * hr/ml) |
| --- | --- |
| Linezolid | 11300 |
| Compound 100 | 16400 |

The metabolic fate of compound 100 as compared to linezolid was analyzed by following excretion of each compound in the urine after intravenous or oral dosing. The results of this analysis are set forth in Table 14.

TABLE 14

Excretion of intact linezolid and compound 100 in urine.

| | Intravenous | | Oral | |
| --- | --- | --- | --- | --- |
| | Male | Female | Male | Female |
| Linezolid | 9290 | 17200 | 13300 | 12800 |
| Compound 100 | 18100 | 35000 | 23900 | 20000 |

The results shown in Table 14 demonstrate that approximately twice as much Compound 100 was excreted intact in the urine as linezolid, regardless of the route of administration or the sex of the subject. In addition, further analysis demonstrated that the amount of the M6 metabolite and its deuterated equivalent were essentially the same, while the amount of deuterated M4 metabolite was significantly lower than the linezolid M4 metabolite.

Figure 15A:
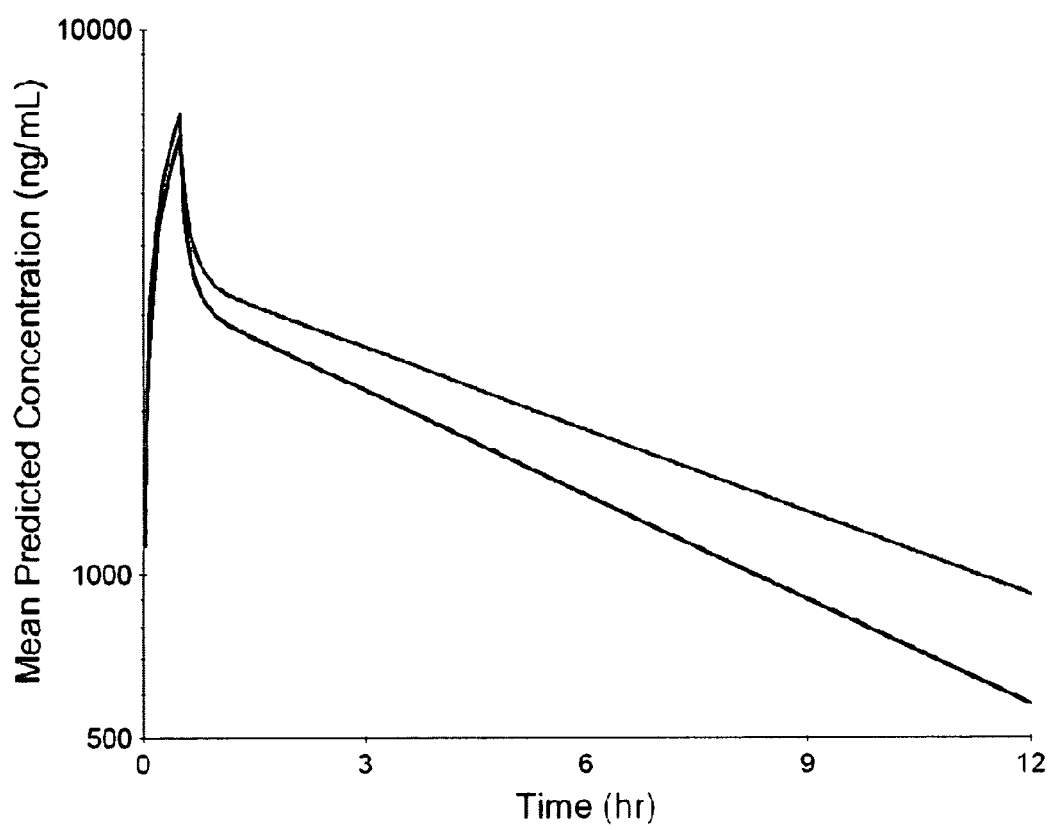
FIG. 15A depicts the serum pharmacokinetics of linezolid and compound 101 following intravenous infusion of a combination of linezolid and compound 101 into a chimpanzee.
Figure 15B:
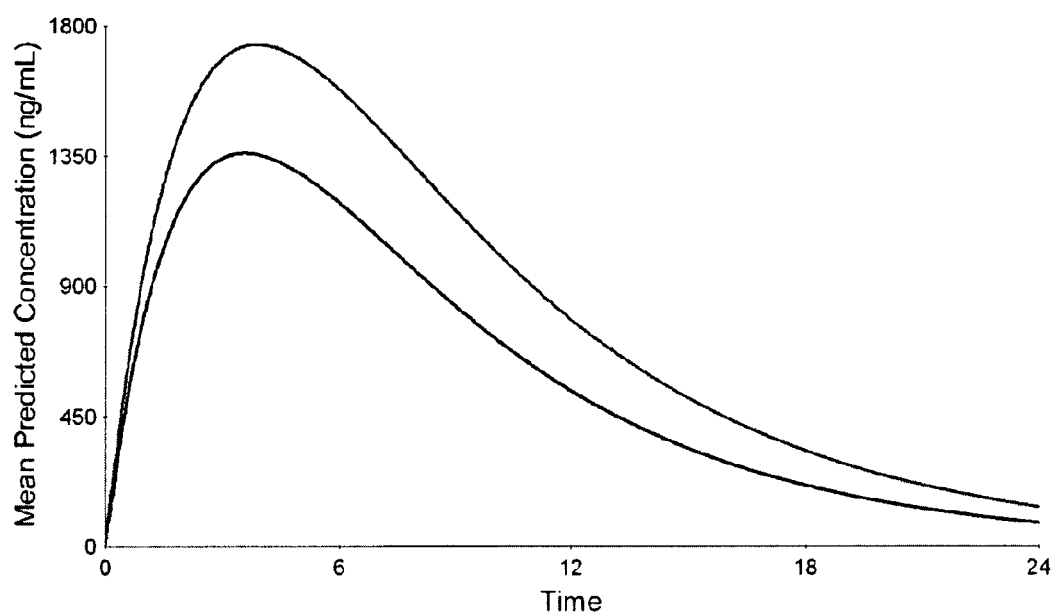
FIG. 15B depicts the serum pharmacokinetics of linezolid and compound 101 following oral administration of a combination of a linezolid and compound 101 into a chimpanzee.

FIG. 15A shows the results of the intravenous dosing study for compound 101 and FIG. 15B shows the results of the oral dosing study for compound 101. The half-life and AUC values for linezolid and compound 101 following intravenous dosing are listed in Table 11. The $C_{max}$ and AUC values for linezolid compound 101 following oral dosing are listed in Table 12.

TABLE 11

Half-life and AUC data for linezolid and compound 101 following intravenous dosing.

| Compound | Half-life (hrs) | AUC (ng · hrs/ml) |
| --- | --- | --- |
| Compound 101 | 6.0 | 30,900 |
| Linezolid | 4.6 | 23,800 |
| % increase | 30% | 31% |

TABLE 12

$C_{max}$ and AUC data for linezolid and compound 101 following oral dosing.

| Compound | $C_{max}$ (ng/ml) | AUC (ng · hrs/ml) |
| --- | --- | --- |
| Compound 101 | 1,880 | 20,600 |
| Linezolid | 1,610 | 15,600 |
| % increase | 22% | 41% |

The chimpanzee studies indicate that compounds 100 is more slowly metabolized than linezolid and that its metabolic fate is shifted away from the M4 metabolite to intact excretion as compared to linezolid. Similar results are observed for compound 101.

In conclusion, a marked potentiation in the stabilization was observed for compounds 100 and 101 when the compounds were studied in primates.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. Various modifications and equivalents can be made without departing from the spirit and scope of the invention.

We claim:

1. A compound of formula I or Ia:

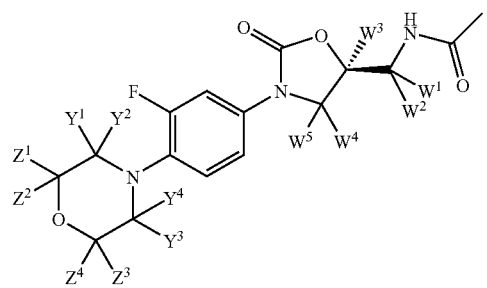

Formula (I)

Formula (Ia)

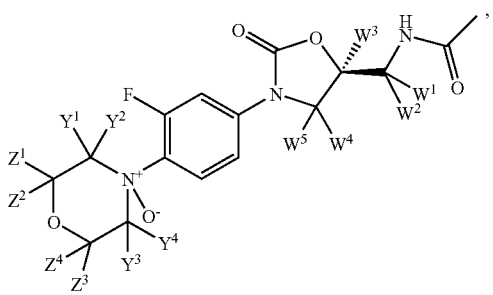

or a pharmaceutically acceptable salt thereof, wherein:
each of $W^1$, $W^2$, $W^3$, $W^4$ and $W^5$ is independently hydrogen or deuterium;
each of $Y^1$, $Y^2$, $Y^3$ and $Y^4$ is independently hydrogen or deuterium;
each of $Z^1$, $Z^2$, $Z^3$ and $Z^4$ is independently hydrogen, deuterium, or fluorine; and
at least one of $W^1$, $W^2$, $W^3$, $W^4$, $W^5$ is deuterium;
at least two of $Y^1$, $Y^2$, $Y^3$ and $Y^4$ are deuterium; and
at least two of $Z^1$, $Z^2$, $Z^3$ and $Z^4$ are deuterium or fluorine.

2. The compound of claim 1, wherein $W^1$ and $W^2$ are simultaneously deuterium.

3. The compound of claim 1, wherein $W^1$ and $W^2$ are simultaneously hydrogen, and no more than two of $Z^1$, $Z^2$, $Z^3$ and $Z^4$ are deuterium.

4. The compound of claim 1, wherein $Y^1$, $Y^2$, $Y^3$ and $Y^4$ are simultaneously deuterium.

5. The compound of claim 1, wherein each of $Z^1$, $Z^2$, $Z^3$ and $Z^4$ is independently selected from deuterium and fluorine.

6. The compound of claim 5, wherein $Z^1$, $Z^2$, $Z^3$ and $Z^4$ are simultaneously deuterium.

7. The compound of claim 1, wherein the configuration of the compound of Formula I or Ia is (S).

8. The compound of claim 1, wherein the compound is

Compound 100

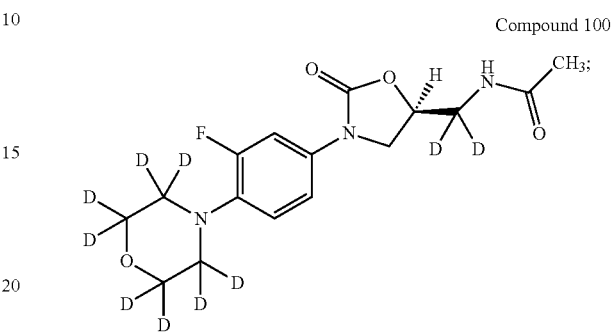

or a pharmaceutically acceptable salt thereof.

9. The compound of claim 1, wherein any atom not designated as deuterium is present at its natural isotopic abundance.

10. The compound of claim 8, wherein any atom not designated as deuterium is present at its natural isotopic abundance.

* * * * *

UNITED STATES PATENT AND TRADEMARK OFFICE
CERTIFICATE OF CORRECTION

PATENT NO. : 8,796,267 B2  
APPLICATION NO. : 12/214260  
DATED : August 5, 2014  
INVENTOR(S) : Tung et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1193 days.

Signed and Sealed this  
Eleventh Day of August, 2015

Michelle K. Lee  
*Director of the United States Patent and Trademark Office*